United States Patent
Mertz et al.

(10) Patent No.: US 7,355,697 B2
(45) Date of Patent: Apr. 8, 2008

(54) FLOW-THROUGH, THERMAL-EXPANSION-COMPENSATED CELL FOR LIGHT SPECTROSCOPY

(75) Inventors: Edward L. Mertz, Washington, DC (US); James V. Sullivan, Bowie, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 418 days.

(21) Appl. No.: 10/926,405

(22) Filed: Aug. 26, 2004

(65) Prior Publication Data

US 2006/0044554 A1  Mar. 2, 2006

(51) Int. Cl.
*G01N 33/20* (2006.01)
(52) U.S. Cl. ...................... 356/246; 356/440
(58) Field of Classification Search ............... 356/244, 356/246, 440, 409, 413; 250/343; 422/102, 422/104
See application file for complete search history.

(56) References Cited

U.S. PATENT DOCUMENTS

| | | | | |
|---|---|---|---|---|
| 4,580,901 A | * | 4/1986 | Goldsmith | 356/409 |
| 4,707,086 A | * | 11/1987 | Dahan et al. | 359/398 |
| 4,804,267 A | * | 2/1989 | Greenfield | 356/335 |
| 4,855,987 A | | 8/1989 | Versluis | |
| 4,974,952 A | * | 12/1990 | Focht | 359/398 |
| 5,170,286 A | * | 12/1992 | Zimmerberg et al. | 359/398 |
| 5,223,716 A | * | 6/1993 | Rossiter | 250/343 |
| 5,552,321 A | * | 9/1996 | Focht | 435/286.1 |
| 5,764,355 A | * | 6/1998 | Gagnon et al. | 356/244 |
| 5,982,488 A | | 11/1999 | Shirasaki | |
| 6,188,474 B1 | * | 2/2001 | Dussault et al. | 356/246 |
| 6,490,034 B1 | | 12/2002 | Woias et al. | |

FOREIGN PATENT DOCUMENTS

| | | |
|---|---|---|
| DE | 41 37 060 A1 | 5/1993 |
| GB | 2071355 A | 9/1981 |
| GB | 2261285 A | 5/1993 |

OTHER PUBLICATIONS

N.N. Kal'nin and S.Y. Ven'yaminov, Zhurnal Prikladnol Spectroskopil, v. 49(4), pp. 592-597 (1988) (English translation).
Attenuated Total Reflectance (ATR) Accessories, Thermo Electron Corporation, http://www.thermo.com/com/CDA/Category/Category_Header/1,2215,23,00.html, accessed Aug. 26, 2004.
Thermo Electron Corporation, http://www.thermo.com/com/CDA/Category/CategoryXtree/0,2212,T-23,00.html, accessed Aug. 26, 2004.

(Continued)

*Primary Examiner*—Hoa Q. Pham
(74) *Attorney, Agent, or Firm*—Venable LLP; Michael A. Gollin; Lars H. Genieser

(57) ABSTRACT

Optical cells are non-actively compensated to ensure that a sample gap of a sample space remains nearly constant upon a change in temperature. Fluids can be flowed through the sample space of the optical cells.

48 Claims, 7 Drawing Sheets

OTHER PUBLICATIONS

Thermo Electron Corporation, http://www.thermo.com/com/CDA/Category/All_Sub_Child_Category/0,2211,23,00.html, accessed Aug. 26, 2004.

N.J. Harrick, Internal Reflection Spectroscopy, Harrick Scientific Corporation, Ossining, New York (1987) (only cover and inside cover pages provided).

Bruker Optics, BioATRCell™ 1, http://www.brukeroptics.com/proteomics/BioARTCell_I.html, accessed Feb. 6, 2006.

Bruker Optics, CONFOCHECK™, http://www.brukeroptics.com/proteomics/ConfoCheck.html, accessed Feb. 6, 2006.

Bruker Optics, AquaSpec™ http://www.brukeroptics.com/proteomics/AquaSpec.html, accessed Feb. 6, 2006.

International Search Report and Written Opinion for PCT/US2005/030218 with 2 cited documents.

* cited by examiner

FLOW-THROUGH, THERMAL-EXPANSION-COMPENSATED CELL FOR LIGHT SPECTROSCOPY

BACKGROUND OF THE INVENTION

1. Field of the Invention

The present invention relates to an optical cell. More particularly, the invention provides a flow-through optical cell in which changes in the dimension of component materials induced by changes in temperature are non-actively compensated to ensure that a sample gap of the sample space remains nearly constant, permitting reproducible spectroscopy despite variations in temperature.

2. Description of the Related Art

Prior optical cells do not mitigate effects of linear expansion of their components, such as U.K. Published Patent Application Number 2,071,355. Some prior optical cells have other problems, such as U.S. Pat. No. 6,490,034 to Woias and Hillerich, in which the optical path length within the cell is not adjustable.

Prior optical cells also do not permit ready sample placement and change of fluids in the sample space. See "Quantitative Measurement of the IR Spectra of Water Solutions" by N. N. Kal'nin and S. Yu Ven'yaminov, Zhurnal Prikladnoi Spektroskopii, 49(4) (1988) pp. 592-597. Only one sample gap distance can be achieved with a given base; a separate base must be machined for each sample gap to be investigated. Because there are no inlets in the cover or in the well, once a sample is contained in the sample space, bath fluid or a fluid sample in the sample space cannot be exchanged with another bath fluid or fluid sample without separating the cover and the base, introducing reproducibility. See also U.K. Published Patent Application Number 2,261,285, which uses solid samples sealed in a silicon-based sample space.

Light spectra of certain samples can be obtained with the attenuated total reflection technique (ATR). The ATR technique has several drawbacks. For example, only samples that can be brought into close contact with the optical element can be investigated; among solid samples, only samples that can be polished very flat can be studied. Investigation of solid samples with an irregular surface with ATR can be difficult or impossible.

SUMMARY OF THE INVENTION

The invention provides an optical cell that is spectroscopically stable, and can be used for spectroscopic measurement in transmission, sample reflection, back plate reflection, emission, or scattering modes. The inventive cell allows fluid in a sample space to be exchanged without separating a front or a back plate from a spacer, allows a solid sample to be placed in or removed from the sample space, requires only a small amount of sample, and allows for different sample gaps to be easily and inexpensively set. The inventive cell and methods allow spectral measurements to be taken over wavelengths ranging at least from the mid-infrared to the vacuum ultraviolet, provide a simple path for light traveling through a sample, and allow fast kinetic processes to be detected and monitored reproducibly and sensitively.

An embodiment of an optical cell of the present invention includes a front plate having a first optical window through which an incident light beam can pass, a back plate, a spacer in contact with the front plate and the back plate, and a frame. The spacer can be separable from the front plate and the back plate. The front and back plates and the spacer can define a sample space capable of containing a sample and having a sample gap between the front plate and the back plate. The frame can be in contact with the front plate and with the back plate. The front plate, back plate, spacer, and frame can be selected to have coefficients of linear expansion and height dimensions so that the optical cell is spectroscopically stable. The back plate can include a second optical window. The volume of the sample space can be less than or equal to about 20 microliters, or can be less than or equal to about 5 microliters. The sample gap can be in a range of from about 0.1 µm to about 3 µm. The smallest dimension of the sample space in a plane parallel to the first optical window can be at least about five times the sample gap.

In the optical cell of the present invention, a sample that includes a solid can be placed into and removed from the sample space. The front plate, back plate, and spacer can containing a solid sample or a gel sample within the sample space. The sample space may receive a liquid sample. The optical cell can include at least one fluid inlet, and a liquid sample can flow through the fluid inlet, into the sample space, and out of the sample space.

The front plate, back plate, spacer, and frame can be selected to have coefficients of linear expansion and height dimensions so that the sample gap changes with temperature by no more than 5 nm per Kelvin temperature change of the sample space in a temperature range of spectroscopic measurement. The linear expansion and height dimensions can further be selected so that the sample gap changes with the sample space temperature by no more than 3 nm per Kelvin or even by no more than 1 nm per Kelvin.

The frame can include a holder, a compensating plate, and a compression plate; the front plate, back plate, spacer, holder, compensating plate, and compression plate can be selected to have coefficients of linear expansion and height dimensions so that the sample gap changes with temperature by no more than 3 nm per Kelvin temperature change of the sample space. The frame can further comprise a first outer gasket and a second outer gasket, which can be selected to have coefficients of linear expansion and height dimensions so that the sample gap changes with temperature by no more than 3 nm per Kelvin temperature change of the sample space.

The front plate, back plate, spacer, and frame can be selected to have coefficients of linear expansion and height dimensions so that the difference between the maximum sample gap and the minimum sample gap during a temperature change of 50 K is no greater than 80 nm, or even no greater than 10 nm.

The first optical window can include one or more of calcium fluoride, magnesium fluoride, barium fluoride, zinc selenide, and diamond. A second optical window can include one or more of calcium fluoride, magnesium fluoride, barium fluoride, zinc selenide, and diamond. The spacer can include at least one of silicone vacuum grease, fluorinated silicone vacuum grease, polytetrafluoroethylene, polyethylene terephthalate, polyethylene, and polypropylene. The holder, the compression plate, and the compensating plate can each include red brass, brass, copper, zinc, aluminum, steel, or an alloy including one or more of these metals or alloys. The compression plate can be formed of the same material as the holder. The first outer gasket and the second outer gasket can each include one or more of aluminum, gold, silver, copper, or an alloy including one or more of these metals.

The optical cell can include a heating/cooling element. The heating/cooling element can include a Peltier plate.

A spectroscopy system, can include the optical cell of claim 1 and a spectrometer; the spectrometer can directs an incident light beam onto a sample contained within the sample space and can receive light transmitted, reflected, or emitted by the sample. The spectrometer of the spectroscopy system can identify a kinetic process occurring on or within the sample with a process time of less than or equal to about 0.2 seconds, or even less than or equal to about 0.001 seconds.

The optical cell according to the present invention can be mounted in a microscope mounting.

A method for obtaining an optical spectrum of a sample can include placing the sample in the sample space, the sample space having a thermomechanically stable sample gap between the first optical window in the front plate and the back plate, directing an incident light beam to pass through the first optical window and into the sample space to impinge on the sample, and measuring the spectrum of light transmitted through, reflected by, emitted by, or scattered by the sample. The incident light beam can be directed to impinge directly on the sample in the sample space without being reflected by the back plate or by the spacer before impinging on the sample. The light transmitted through, reflected by, emitted by, or scattered by the sample can be reflected at most once by the back plate or by the spacer while traveling through the sample. The incident light beam can contain light having a wavelength in the range of from about 0.1 μm to about 50 μm.

A method for obtaining an optical spectrum of a sample can include measuring the infrared, visible, or ultraviolet spectrum of light transmitted through, reflected by, emitted by, or scattered by a sample. A method can include measuring the Raman spectrum of light scattered by a sample.

In a method for obtaining an optical spectrum of a sample, the incident light beam can be directed to pass through the first optical window into the sample space with an angle of incidence at an interface between the first optical window and the sample space less than or equal to about 95% of the critical angle.

In a method for obtaining an optical spectrum of a sample, a bath fluid in the sample space can be exchanged within less than or equal to about 0.2 seconds. The sample can comprise a solid and the spacer can be separated from the front plate or from the back plate to place a sample in or to remove a sample from the sample space.

In a method for obtaining an optical spectrum of a sample, a heating/cooling element in contact with the frame can be provided, and the temperature of the heating/cooling element can be ramped according to a predetermined schedule while measuring the spectrum of light transmitted through, reflected by, emitted by, or scattered by the sample.

DETAILED DESCRIPTION

Figure 1:
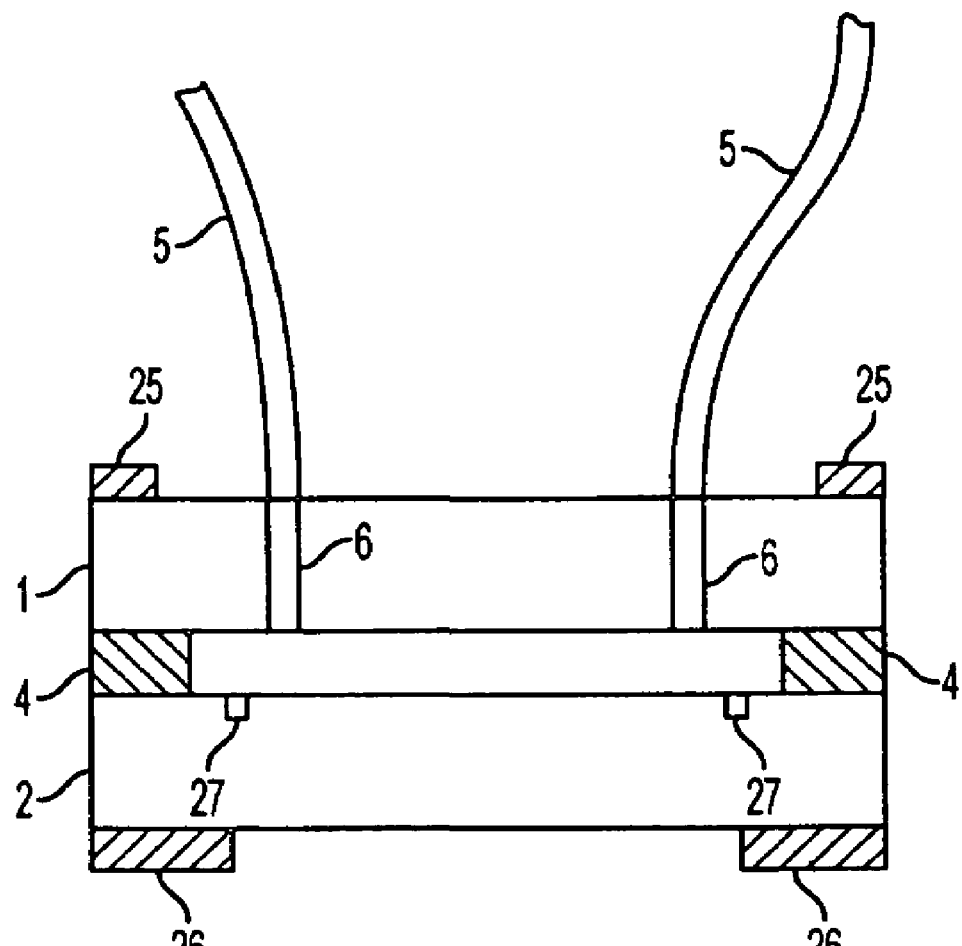
FIG. 1 is a cross-sectional schematic detail of a front plate, a spacer, a back plate, and other components of a flow-through, thermal-expansion-compensated cell for light microscopy according to an embodiment of the invention.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without parting from the spirit and scope of the invention. All references cited herein are incorporated by reference as if each had been individually incorporated.

Optical cells for holding samples, controlling conditions such as bath fluid and temperature around a sample, and having excellent spectroscopic stability are required for a wide variety of experimental and analytical techniques. The invention provides spectroscopically stable optical cells for holding samples and controlling conditions such as bath fluid and temperature around a sample, for a wide variety of experimental and analytical techniques. Spectroscopic stability refers to the ability of an optical cell of the invention to permit the measured spectrum of a sample to be substantially constant when experimental conditions, for example, the surrounding bath fluid or temperature of the sample, are changed, without introducing artifacts. Spectroscopic stability permits accurate measurement of changes in the sample spectrum that occur due to changes in the experimental conditions such as temperature change. For example, spectroscopic stability is present when the absorbance of peaks in a spectrum of a solid sample measured in an optical cell has a small standard deviation over several measurements in which bath fluid is exchanged. Spectroscopic stability can relate to the measured spectrum of a sample being substantially constant (or changes in the sample spectrum being accurately measured) over a period of time in which experimental conditions, such as temperature and the bath fluid, are held constant. Details of the reproducibility provided by embodiments of the optical cell of the invention are discussed below. In a spectroscopically stable optical cell of the invention, a difference spectrum derived from spectra obtained at a lower temperature and at a higher temperature exhibits no or insignificant artifactual peaks. Spectroscopic stability can refer to a trace component peak of small absorbance being distinguishable in a difference spectrum derived from a spectrum of a solution including the trace component and a solvent and a spectrum of the solvent.

An aspect of spectroscopic stability is thermomechanical stability of a sample gap of an optical cell of the invention, as discussed below. A thermomechanically stable sample gap does not vary more than a few nanometers in size per Kelvin of temperature variation, due to the selection and dimensions of the optical cell components. By maintaining a constant sample gap, the inventive optical cells limit spectroscopic artifacts due to a sample space temperature change or over a period of time in which experimental conditions, such as bath fluid, are held constant.

The spacer can have a thickness in the range of, for example, between about 0.1 μm, 0.2 μm, 0.3 μm, 0.5 μm, 1 μm, 3 μm, 5 μm, 10 μm, 15 μm, 20 μm, 50 μm, 100 μm, or 1000 μm, providing a sample gap of similar size. The working temperature range of the sample space can be, for example, at least about or at most about −10° C., 5° C., 60° C., or 100° C.

The incident light beam can include light of wavelength in the range of, for example, between about 0.1 μm, 0.12 μm, 0.15 μm, 0.5 μm, 7 μm, 10 μm, 22 μm, or 50 μm. The optical windows can transmit light of these wavelengths.

The optical windows can have a thickness in the range of, for example, at least about or at most about 0.5 mm, 1 mm, 2 mm, 3 mm, 5 mm, or 10 mm.

The sample gap can exhibit a change with the temperature in the sample space in the range of, for example, at most about 0.6 nm/K, 0.9 nm/K, 1 nm/K, 2.1 nm/K, 2.4 nm/K, 3 nm/K, or 5 nm/K. The sample gap can exhibit a change with a 50 K temperature change in the sample space in the range of, for example, at most about 10 nm, 80 nm, or 160 nm. The sample gap can exhibit a change with a 30 K temperature change in the sample space in the range of, for example, at least about or at most about 5 nm, 10 nm, 20 nm, 30 nm, 50 nm, 60 nm, or 100 nm.

Prior art optical cells exhibit time-dependent change in the sample gap. If an optical cell is assembled at a first temperature, say room temperature, and then a second temperature is used in an experiment, the sample gap may continue to slowly change over a long period of time at the second temperature. This problem of a long duration, slow change in time can be ameliorated by annealing; that is, the optical cell can be held at a given temperature for a period of time or repetitively thermally cycled over a period of time prior to use in an experiment. However, prior art optical cells require one to two days of annealing, resulting in a severe limit on the rate at which experiment can be performed and data can be acquired.

By contrast, an optical cell according to the present invention can require less than an hour of annealing time for the sample gap to be stable over a long period of time.

For example, over a two week period during which the temperature in the sample space remains constant, the sample gap can be stable within the range of about 0.5 nm to about 5 nm.

A liquid in the sample space can be exchanged with another liquid in a time in the range of, for example, between about 0.001 seconds, 0.06 seconds, 0.1 seconds, or 0.2 seconds. A kinetic process occurring on or within a sample in the sample space can be detected which occurs over the same time scale. The characteristic width of a light spot on the sample resulting from an incident light beam can be in the range of, for example, between about 5 μm, 2 μm, 1.3 μm, 0.5 μm, or 1 mm. The size of the sample can be, for example, between about 1 μm, 3 μm, 10 μm, 50 μm, 100 μm, 150 μm, 1 mm, 5 mm, or 10 mm.

Over a two week period during which the temperature of a water sample in the sample space remains constant, the 1644 cm−1 peak in the water spectrum with an absorbance of 0.5 absorbance units can be stable within the range of, for example, at most about $1\times10^{-4}$ absorbance units, $2.5\times10^{-4}$ absorbance units, or $5\times10^{-4}$ absorbance units.

A spectroscopic system including an optical cell according to the present invention can identify N-methyl-formamide in water with the N-methyl-formamide at a concentration in the range of, for example, at least about or at most about 0.002 vol %, 0.005 vol %, or 0.01 vol %. A spectroscopic system including an optical cell according to the present invention can identify a marker peak of a trace component in a solution of a solvent and the trace component, a solvent masking peak exhibiting absorption of from about 0.3 to about 0.5 absorption units when the absorption of the marker peak is in the range of, for example, at least about or at most about $1\times10^{-4}$, $1.5\times10^{-4}$, $2\times10^{-4}$, or $1\times10^{-3}$.

Upon changing a fluid in a sample space 32 of an optical cell according to the present invention can allow detection of change in absorbance of the sample in the range of, for example, between about $1\times10^{-4}$ absorbance units, $5\times10^{-3}$ absorption units, 0.01 absorbance units, 0.1 absorbance units, or 1 absorbance unit.

A spectroscopic system including an optical cell according to the present invention can determine the ratio of absorbance of two peaks of a gel sample, lying within the range of 2000 cm−1 to 700 cm−1, each peak having an absorbance in the range of from 0.3 to 1.5 absorbance units, when the bath fluid is changed four times and the spectrum measured initially and after each change, so that the standard deviation of the peak ratio can be in the range of, for example, between about 0.03%, 0.3%, 3%, or 30%.

A calculated normalized difference spectrum variation in measurements obtained with a water sample with sample gaps in the range from 0.5 μm to 15 μm in an optical cell according to the present invention can be in the range of, for example, at least about or at most about 0.05, 0.25, or 0.8. A calculated normalized difference spectrum variation in measurements obtained with an air sample with sample gaps in the range from 0.5 μm to 15 μm in an optical cell according to the present invention can be in the range of, for example, between about 0.02, 0.04, 0.23, or 0.65.

In an embodiment of a thermal-expansion-compensated cell according to the present invention, shown in FIG. 1, a front plate 1 and a back plate 2 are in contact with and separated by a spacer 4. The front plate 1 includes a first optical window. The first optical window can form part of the front plate 1; alternatively, the first optical window can form all of the front plate 1, as shown in FIG. 1. The back plate 2 need not, but can include a second optical window.

Figure 2:
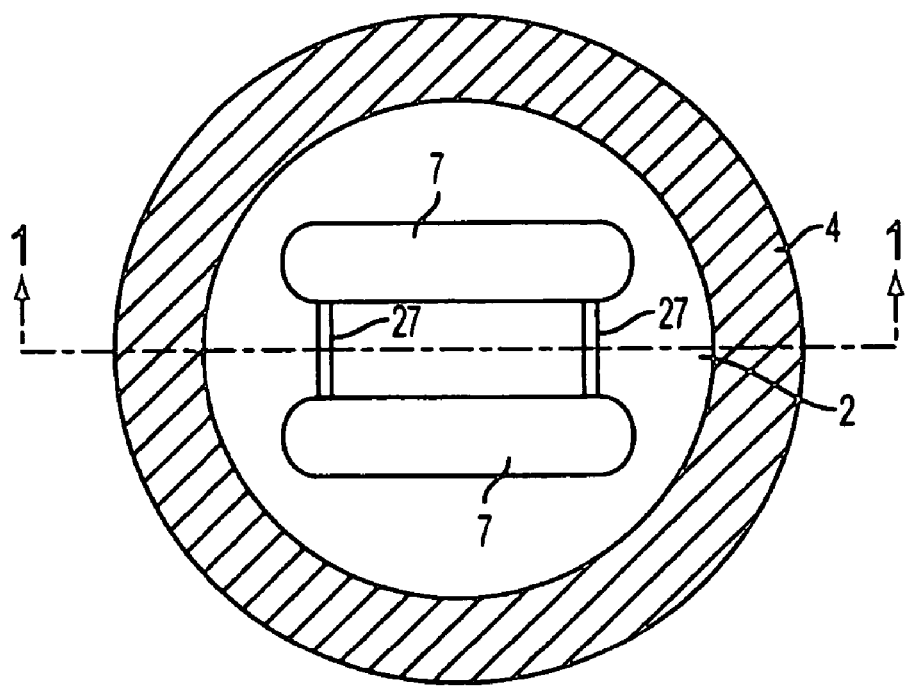
FIG. 2 is a top view of a spacer and a back plate with grooves of a flow through, thermal-expansion-compensated cell for light microscopy according to an embodiment of the invention.
Figure 6:
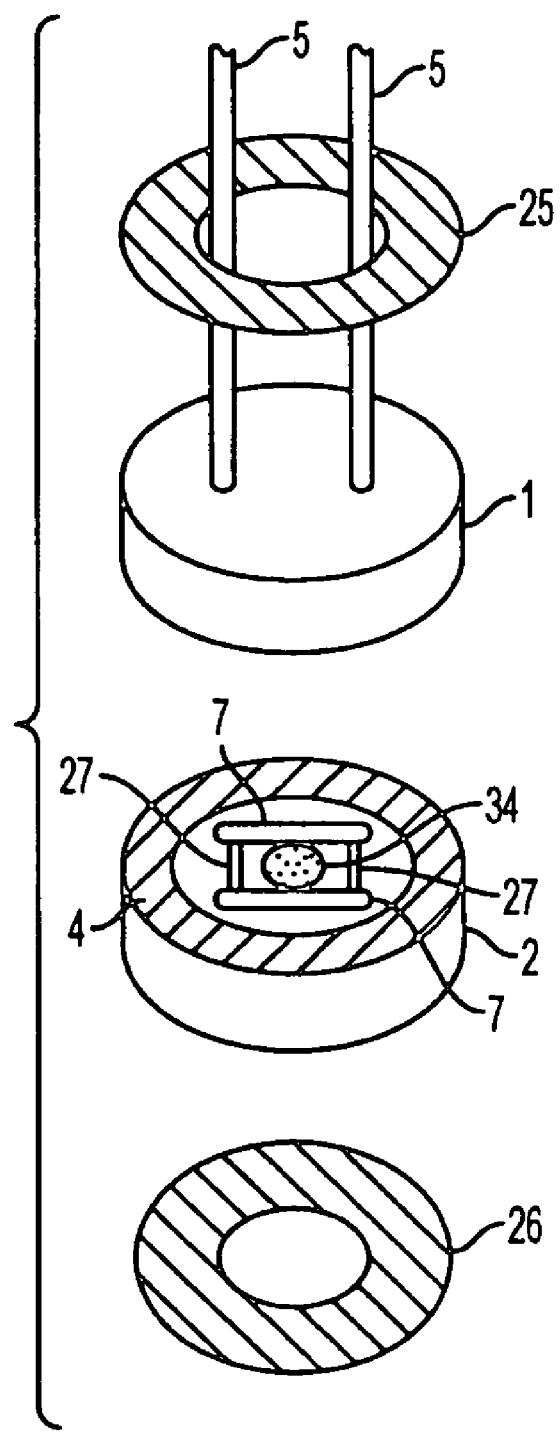
FIG. 6 is an exploded perspective view of a front plate, a spacer, a back plate, a solid or gel sample, fluid tubes, a first outer gasket, and a second outer gasket of a flow-through, thermal-expansion-compensated cell for light microscopy according to an embodiment of the invention.

The front plate 1 can be adjacent to a sample space 32; the front plate 1, the back plate 2, and the spacer 4 can bound the sample space 32. The front plate 1 can have one or more fluid inlets 6, through which a fluid can enter the sample space 32 from the environment or exit the sample space 32. The back plate 2 can have one or more fluid inlets; the spacer 4 can have one or more fluid inlets. Fluid can be guided towards a fluid inlet 6 or away from a fluid inlet 6 with fluid tubes 5. The back plate 2 and/or the front plate 1 can have one or more grooves 7, as shown in FIG. 2 and FIG. 6. The grooves can be parallel. For example, the two fluid inlets 6 can be in the front plate 1, as illustrated in FIG. 1, two parallel grooves 7 can be carved onto the back plate 2, as illustrated in FIGS. 2 and 6, and two connector channels 27 that link the two parallel grooves 7 can be carved onto the back plate 2, as illustrated in FIGS. 1, 2 and 6. The front plate 1 and the back plate 2 can be oriented with respect to each other so that the two fluid inlets 6 in the front plate 1 are above the region between the two parallel grooves in the back plate 2, as illustrated in FIG. 6.

Any one or any combination of a range of transparent materials can be used to form the first optical window of the front plate 1, for example, calcium fluoride, magnesium fluoride, barium fluoride, zinc selenide, germanium, fused silica, borosilicate glass, quartz, or sapphire and other materials as would be recognized by a person of skill in the art. Diamond can also be used to form the first optical window, for example, for high pressure experiments. The back plate 2 can be transparent or can include a second optical window for use of the optical cell in a transmission mode, or the back plate 2 can be opaque for use of the optical cell in a reflection mode, as described below. A second optical window can be formed of, for example, calcium fluoride, magnesium fluoride, barium fluoride, zinc selenide, germanium, fused silica, borosilicate glass, quartz, sapphire, diamond, and other materials as would be recognized by a person of skill in the art. If a front plate 1 or a back plate 2 is not entirely formed of a first optical window or second optical window, the part of the front plate 1 or the back plate 2 that is not a window can be formed of, for example, any one or any combination of materials including red brass, brass, copper, zinc, aluminum, steel, a metal, and an alloy. The front plate 1 and the back plate 2 preferably do not comprise crystalline silicon. The selection of a material to form a part of a front plate 1 or a back plate 2 that is not a window can, for example, be based on the coefficient of linear expansion. Additional characteristics that may influence the selection of a material include, for example, thermal conductivity, modulus of elasticity, and yield strength. For example, if a sample will be subjected to a high pressure, it may be preferable to form a part of a front plate 1 or a back plate 2 that is not a window from steel. The spacer 4 can be formed from any one of a range of materials or combination of materials. Preferably, the spacer is formed of a material or materials which are continuous around the sample gap.

Figure 3:
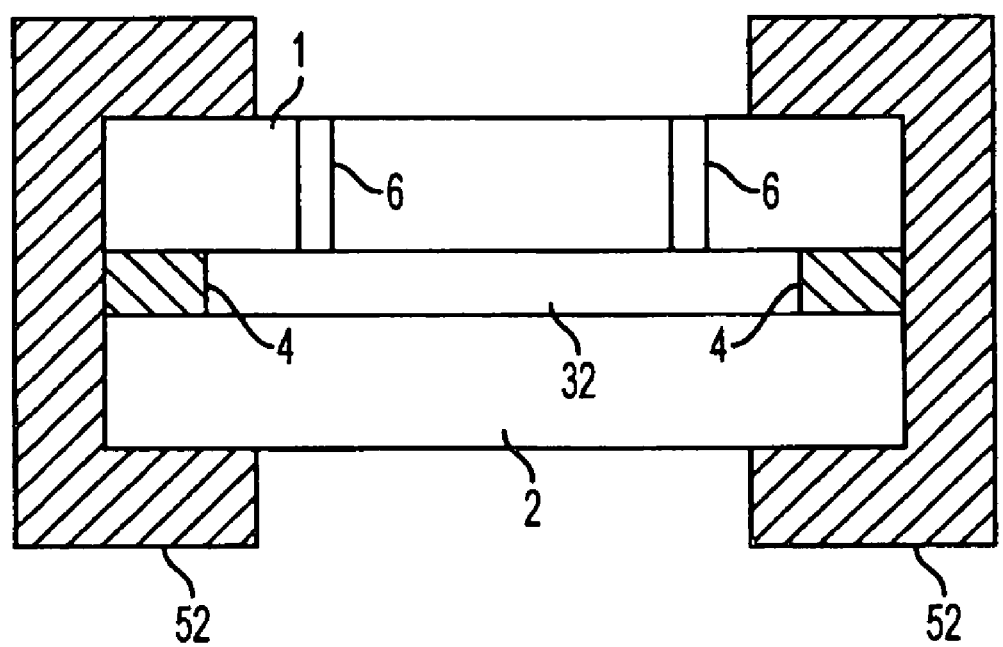
FIG. 3 is a cross-sectional schematic detail of a front plate, a spacer, a back plate, and other components contained in a frame of a flow-through, thermal-expansion-compensated cell for light microscopy according to an embodiment of the invention.
Figure 4:
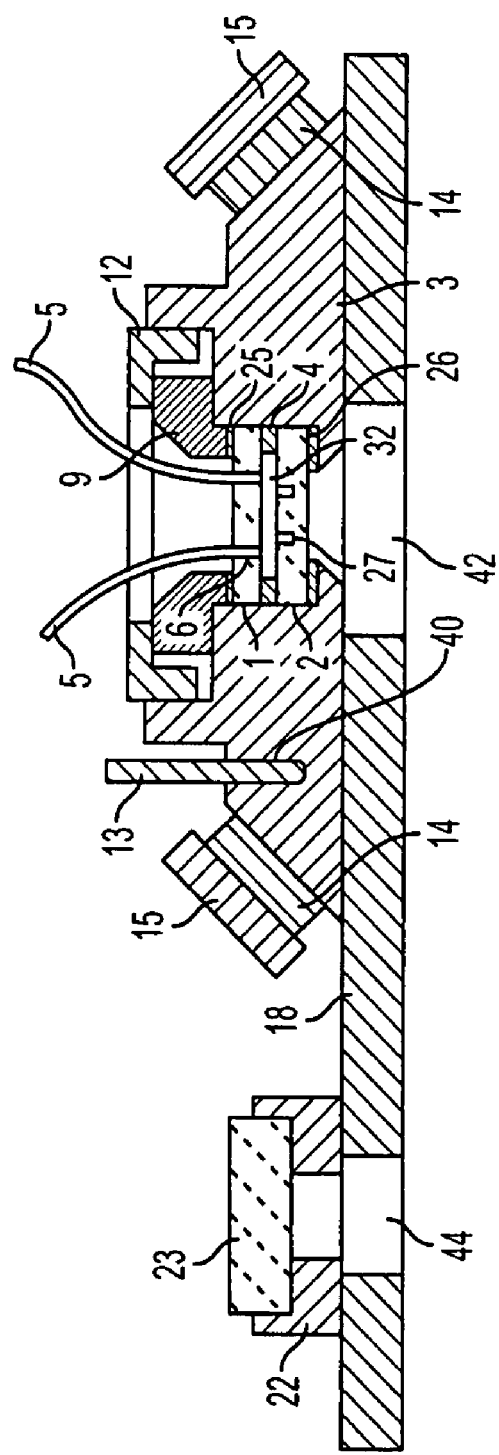
FIG. 4 is a cross-sectional schematic detail of a front plate, a spacer, a back plate, and other components contained in a holder, mounted for use as a flow-through, thermal-expansion-compensated cell for light microscopy according to an embodiment of the invention.

The front plate 1 with two fluid inlets 6, the back plate 2, and the spacer 4 can be contained in a frame 52, as shown in FIG. 3. The frame 52 can be in contact with the front plate 1 and the back plate 2. The frame 52 can be designed to allow removal and replacement of the front plate 1, the back plate 2, and the spacer 4, and the frame can be formed of two or more separable parts. For example, the frame 52 can include a holder 3 and related parts, as shown in FIG. 4. The holder 3 can be in contact with the back plate 2; alternatively, a second outer gasket 26 can be between and in contact with each of the holder 3 and the back plate 2. A compensating plate 9 can be contained in the holder 3 and can be in contact with the front plate 1. Alternatively, a first outer gasket 25 can be between and in contact with each of the compensating plate 9 and the front plate 1. The first outer gasket 25 and the second outer gasket 26 are illustrated in FIGS. 1 and 6 as well as in FIG. 4.

As further shown in FIG. 4, the holder 3 can be in contact with the compensating plate 9. The holder 3 can have one or more pins pointing in the direction of the compensating plate 9. The compensating plate 9 can have one or more bores for receiving the pins of the holder 3.

A compression plate 12 can be in contact with compensating plate 9 and holder 3. For example, an outer circumference of compression plate 12 can be threaded, and an inner circumference of holder 3 that the compression plate contacts can have corresponding threads to allow for close and secure contact between compression plate 12 and holder 3.

Holder 3, compensating plate 9, and compression plate 12 can be formed of any one or any combination of materials including red brass, brass, copper, zinc, aluminum, steel, a metal, an alloy, or any other material appearing useful to one skilled in the art. The compression plate 12 can be formed of the same material as the holder 3, which can be advantageous in non-actively compensating for the effect of temperature on the dimensions of the components of the optical cell. In an embodiment, the compensating plate 9 and the compression plate 12 can be included in a single component. Any one or any combination of a range of materials can be used to form the first outer gasket and to form the second outer gasket, including aluminum, gold, silver, copper, a metal, an alloy, or any other material appearing useful to one skilled in the art. The first outer gasket and the second outer gasket may be formed of the same or of different materials.

A thermal probe 13 can measure the temperature of the holder 3. A probe bore 40 can receive the thermal probe 13. The thermal probe 13 can be, for example, an expansion thermometer, such as a mercury thermometer, a thermocouple, or a resistance temperature detector, such as a metal resistance thermometer or a thermistor. A heater/cooler can regulate the temperature in the sample space 32. For example, one or more Peltier plates 14 for controlling temperature can be in contact with holder 3, and/or heat sink 15, which improves the heat transfer performance of Peltier plate 14. The heat sink 15 can, for example, have a heat transfer fluid, such as water, circulating through it.

The holder 3 can be in contact with a mounting plate 18. The mounting plate 18 can have a holder bore 42 that can allow light traveling out of the back plate 2 and towards the mounting plate 18 to travel beyond the mounting plate 18 so that characteristics of the light, for example, the spectrum or the polarization, can be measured. Alternatively, instead of holder 3 being in direct contact with mounting plate 18, a thermal insulator can be placed between holder 3 and mounting plate 18. A thermal insulator can, for example, have the form of a sheet cut into a ring. In the open areas of the ring, where holder 3 and mounting plate 18 are not in contact, air can serve to thermally insulate the holder 3 from the mounting plate 18. Materials that can be used for a thermal insulator, include, for example, polytetrafluoroethylene, a polymer with a softening point greater than a temperature at which the optical cell will be operated, a metal with a low thermal conductivity, or any other material appearing useful to one skilled in the art.

The optical cell can include a reference receptacle 22 that can contain a reference window 23. The reference receptacle 22 can be in contact with or affixed to the mounting plate 18. A reference bore 44 in the mounting plate 18 can allow light traveling out of the reference window 23 and towards the mounting plate 18 to travel beyond the mounting plate 18.

Figure 5:
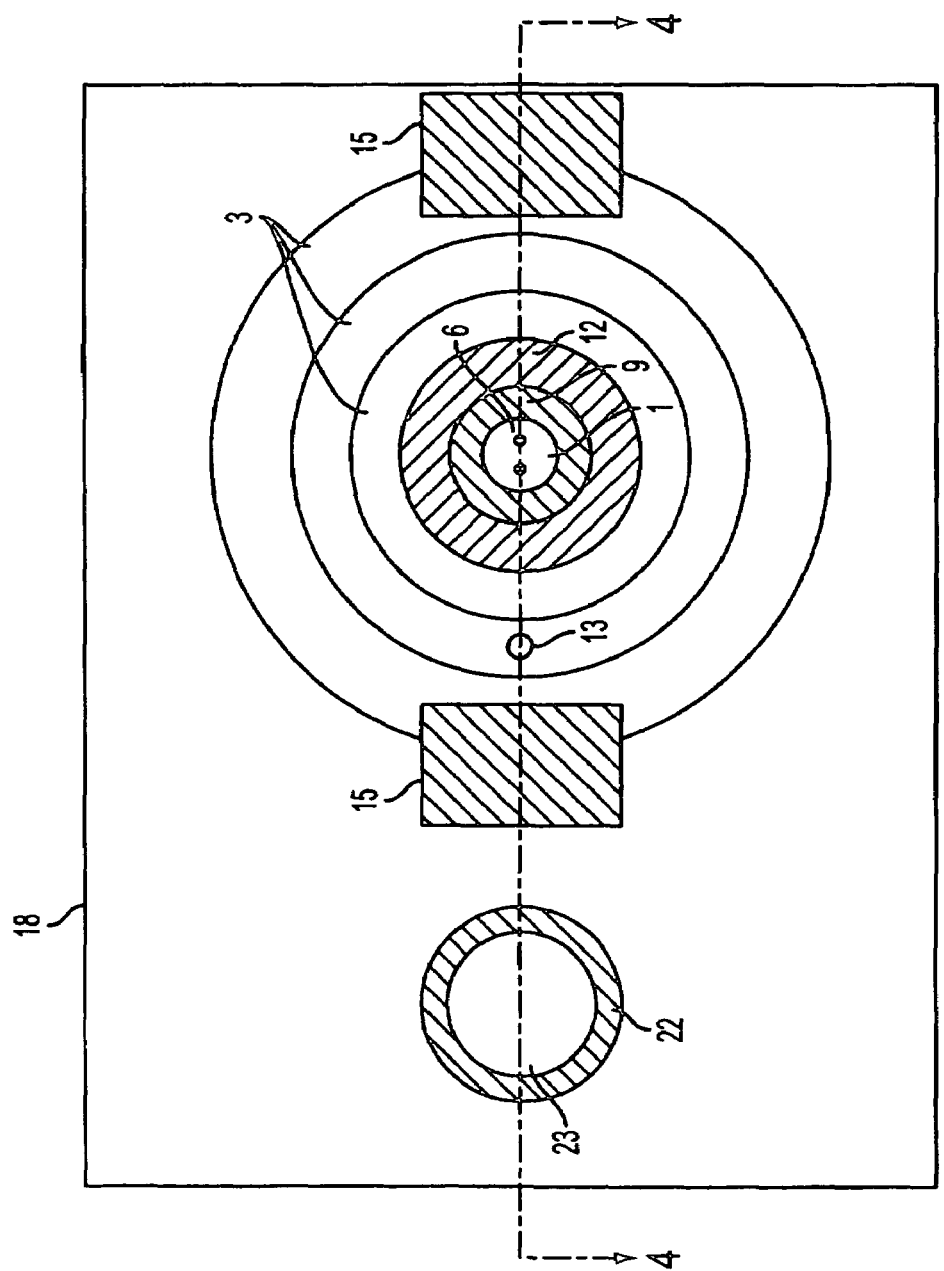
FIG. 5 is a top view of a front plate with fluid inlets, a compensating plate, a compression plate, a holder, and other components mounted for use as a flow-through, thermal-expansion-compensated cell for light microscopy according to an embodiment of the invention.

FIG. 5 shows an optical cell according to the present invention. The front plate 1, compensating plate 9, compression plate 12, holder 3, and mounting plate 18 are illustrated. Fluid inlets 6 in the front plate 1 are shown. The heat sinks 15 and the temperature probe 13 are shown. The reference receptacle 22 and the reference window 23 are shown.

In order to assemble a thermal-expansion compensated cell according to the present invention, the following steps can be performed. The back plate 2 and the spacer 4 can be placed into contact. The front plate 1 can be placed into contact with the spacer 4, so that the front plate 1 and the back plate 2 contact opposite sides of the spacer 4. If a solid or gel sample is to be placed into the sample space 32, the back plate 2 and the spacer 4 can be placed into contact and the solid sample 34 placed onto the back plate 2 before the front plate 1 is placed into contact with the spacer 4. A first outer gasket 25 can be placed into contact with the surface of the front plate 1 facing away from the sample space 32; a second outer gasket 26 can be placed into contact with the surface of the back plate 2 facing away from the sample space 32.

FIG. 6 shows an exploded view of the front plate 1, the spacer 4, a back plate 2 with grooves 7 and connector channels 27, a solid or gel sample 34, the inlet tubes 5, the first outer gasket 25, and the second outer gasket 26. By removing the front plate 1 from the spacer 4, a solid or gel sample 34 can be removed from the sample space.

Figure 7:
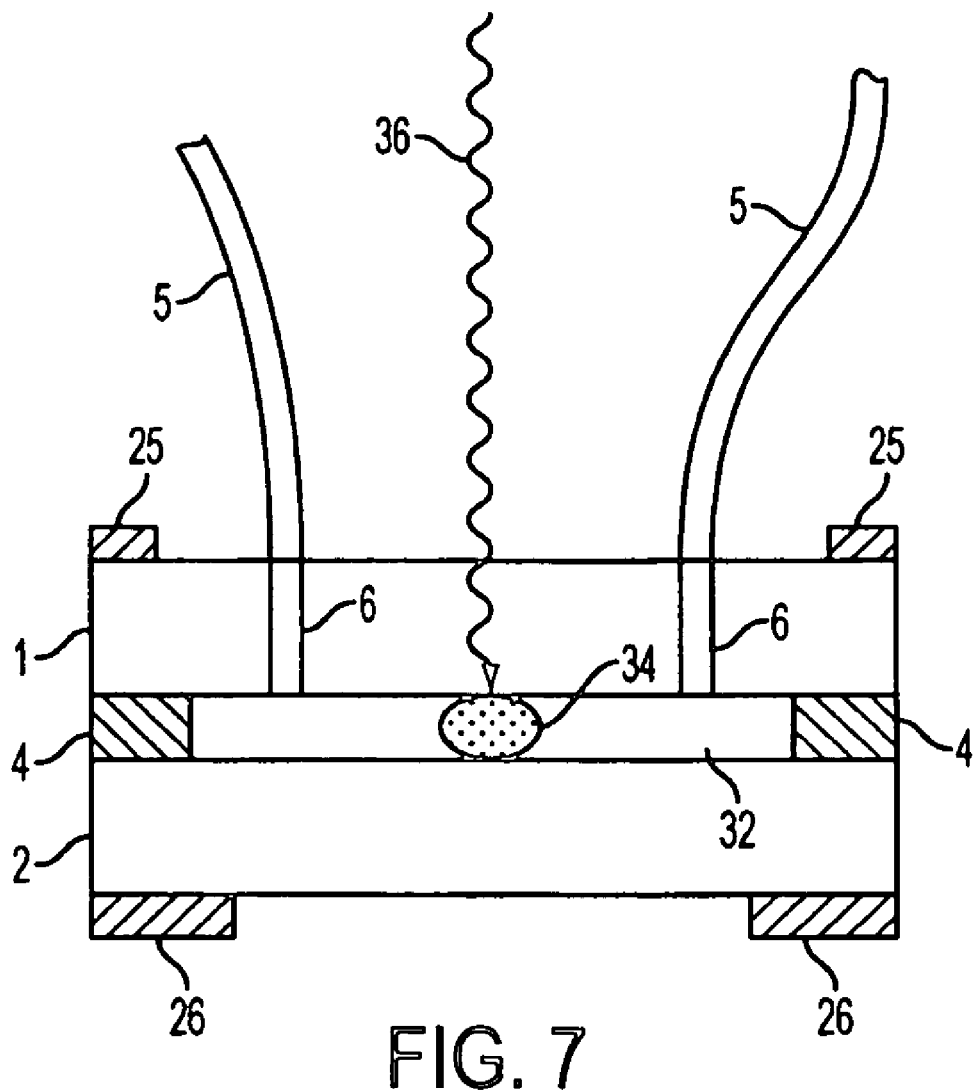
FIG. 7 is a cross-sectional schematic detail of a front plate, a spacer, a back plate, and other components of a flow-through, thermal-expansion-compensated cell for light microscopy according to an embodiment of the invention with a sample in a sample space and an incident light beam impinging on the sample

FIG. 7 shows the front plate 1, the spacer 4, the back plate 2, the sample space 32, the fluid inlets 6, the inlet tubes 5, the first outer gasket 25, the second outer gasket 26 and a solid or gel sample 34 in the sample space 32. An incident light beam 36 is shown impinging on the solid or gel sample 34.

The front plate 1, spacer 4, and back plate 2 can have any one of a number of shapes. For example, the front plate 1, the back plate 2, the first optical window, and a second optical window can be polygonal, e.g., square, circular, elliptical, rectangular, or complex in shape; the front plate 1, the back plate 2, the first optical window, and the second optical window need not have the same shape. The spacer 4, can be, for example, polygonal, e.g., square, rectangular, circular, elliptical, or complex in shape. The sample space 32 can be, for example, polygonal, e.g., square, rectangular, circular, elliptical, or complex in shape. Other components, such as the compensating plate 9, the compression plate 12, and the holder 3, can be of various shapes, for example, polygonal, e.g., square, rectangular, circular, elliptical, or complex in shape; for example, the holder may be rectangular.

The dimensions of a circular optical window can be described in terms of diameter and thickness. The dimensions of an optical window of a different shape can be described in terms of thickness and a characteristic width. It can be useful to take the longest length across a surface of the window as the characteristic width; for example, the diagonal length of a square window can be taken as the characteristic width. Use of a circular first optical window and a circular second optical window may be convenient, because optical windows made of various materials are often mass produced in a circular shape. Windows purchased from optical suppliers can used in an optical cell according to the present invention; no special machining is required. Thus the windows can be relatively inexpensive, and a window can be selected from a wide range of commercially available windows, so that characteristics of a window such as temperature resistance, solvent resistance, refractive index, and transmission of wavelengths of interest can be optimized for a given experiment.

It may be convenient to produce the front plate 1, back plate 2, or spacer 4 with the same shape of the perimeter as the first optical window or as a second optical window; it may be convenient for these components to have a circular perimeter.

The first optical window in the front plate 1 can be selected based on parameters of the experiment to be performed. These may include, for example: (a) the transparency of the first optical window to an incident beam of light having one or a range of wavelengths traveling from the environment, through the first optical window, and into the sample space 32; (b) the transparency of the first optical window to light of wavelengths reflected or transmitted by the sample 34; (c) the resistance of the first optical window to chemical attack by a liquid or solid sample 34 in the sample space 32, to stresses induced by thermal gradients between the sample space 32 and the environment, and to differences in pressure between the sample space 32 and the environment; and (d) the refractive index of the sample or of a bath fluid surrounding the sample can be considered. For example, an optical material can be selected to have a similar refractive index as the sample or as a bath fluid. A second optical window in the back plate 2 can be selected based on experimental parameters.

An optical window may, for example, have a thickness in the range of from about 0.5 mm to about 6 mm, and may have a characteristic width, e.g., a diameter, in the range of from about 3 mm to about 100 mm. Preferably, the thickness may be in the range of from about 1 mm to about 3 mm, and the characteristic width, e.g., a diameter, may be in the range of from about 3 mm to about 32 mm. For example, an optical window can have a thickness of about 2 mm and a diameter of about 13 mm.

The thickness of the spacer 4 can be selected according to the desired sample gap. The spacer 4 can be compressed, for example, by screwing the compression plate 12 into the holder 3, so that the sample gap is less than the initial thickness of the spacer. For example, the sample gap can range from about 0.1 µm to about 1000 µm, preferably from about 0.2 µm to about 100 µm, and most preferably from about 0.3 µm to about 50 µm. For small sample gaps, e.g., of less than about 5 µm, silicone or fluorinated silicone vacuum grease can be used to form the spacer 4. The vacuum grease can be dissolved in a volatile solvent, the vacuum grease solution can be applied near to the edge of a surface of the front plate 1 or the back plate 2, and the solvent allowed to evaporate to form the spacer 4. For larger sample gaps, e.g., of at least about 20 µm, the spacer 4 can be formed of a polymer such as polytetrafluoroethylene, polyethylene terephthalate, polyethylene, or polypropylene, with or without silicone or fluorinated silicone vacuum grease. For intermediate sample gaps, e.g., of from at least about 5 µm up to about 20 µm, the spacer 4 can be formed of silicone or fluorinated silicone vacuum grease and/or a polymer.

A fluid inlet 6 can include a bore which passes from the surface of a front plate 1 or a back plate 2 that faces the environment to the surface of the front plate 1 or the back plate 2 that faces the sample space 32. The axis of the bore can be normal to the surface of the front plate 1 or the back plate 2 that faces the environment. Alternatively, a bore of a fluid inlet may pass from the edge of the front plate 1 or the back plate 2 to the surface of the front plate 1 or the back plate 2 that faces the sample space 32; the axis of the bore may be at a large angle with respect to the normal of the surface of the front plate 1 or the back plate 2 that faces the environment. Alternatively, a fluid inlet may have the form of a trench on the surface of a front plate 1 or a back plate 2 facing the sample space 32. The trench can extend to the edge of the front plate 1 or the back plate 2. Fluid can be provided by such a trench to the sample space 32 through an opening between the spacer 4 and the front plate 1 or the back plate 2.

A fluid tube 5 can be inserted in a fluid inlet 6 of the front plate 1 or of the back plate 2. If fluid is not to be passed into or withdrawn from the sample space 32 after the front plate 1, spacer 4, and back plate 2 are assembled, the fluid inlet or inlets 6 can be plugged.

The front plate 1, spacer 4, and back plate 2 can be placed into a frame 52. For example, the frame 52 can include a holder 3. A second outer gasket 26 can be placed into the holder 3. The spacer 4 and the back plate 2 can be placed into holder 3 and onto second outer gasket 26. The second outer gasket 26 can serve to apply stress imposed by the holder 3 evenly where the second outer gasket 26 contacts the back plate 2. The front plate 1 can be placed onto the spacer 4. A first outer gasket 25 can be placed onto the front plate 1; and the compensating plate 9 can be placed onto the first outer gasket 25. The first outer gasket 25 can serve to apply stress imposed by the compensating plate 9 evenly where the first outer gasket 25 contacts the front plate 1. A compression plate 12 can be placed over the compensating plate 9. The compression plate 12 can be affixed to the holder 3, so that the compression plate 12 applies force to the compensating plate 9. The force applied can be small and sufficient to ensure that the compensating plate 9, first outer gasket 25, front plate 1, spacer 4, back plate 2, second outer gasket 26, and holder 3 remain in contact with each other during an experiment. For experiments in which a sample is subjected to high pressure using, for example, an optical cell with a first optical window of diamond, the force applied can be large. The compression plate 12 can be affixed to the holder 3 by, for example, screwing threads on an outer circumference of the compression plate 12 into corresponding threads on an inner circumference of the holder 3. For example, compression plate 12 can be machined in conjunction with holder 3 to provide a predetermined sample gap when compression plate 12 is screwed into holder 3.

A height direction can be defined as the direction normal to the surface of the first optical window adjacent to the sample space 32 at the center of the first optical window. The sample gap can be defined as the distance in the height direction between the surface of the first optical window adjacent to the sample space 32 at the center of the first optical window and the surface of the back plate 2.

The materials forming front plate 1, spacer 4, back plate 2, first outer gasket 25, second outer gasket 26, compensating plate 9, compression plate 12, and holder 3 and their dimensions are selected according to the invention, so that the sample gap changes only minimally with a change in the temperature in the sample space 32.

The width of the sample space may be wider than the sample gap, for example, the width can be 5, 10, 20, or 50 times wider than the sample gap.

An optical cell according to the present invention can include a sample space 32 with volume less than or equal to about 10,000 microliters (μL). The volume of the sample space may be in the range of from about 0.01 μL to about 100 μL, preferably in the range of from about 0.4 μL to about 20 μL, for example, 2.5 μL.

The holder 3 can be affixed to the mounting plate 18. For example, the holder can have arc-shaped slots, through which screws can fit, and the mounting plate can have threaded holes for receiving the screws. With such a configuration, the screws can be loosened to allow rotation of the holder, and the screws can be tightened to secure the holder to the mounting plate.

An embodiment of an optical cell according to the present invention can be used to obtain an optical spectrum of a sample 34 in the sample space 32. As shown in FIG. 7, an incident light beam 36 can be directed to travel through the first optical window in the front plate 1, enter the sample space 32, and impinge on the sample. The sample can be a liquid, a solid, or an intermediate state such as a gel; a solid or gel sample 34 is illustrated in FIG. 7. A liquid sample can fill a portion of or the entire sample space 32. A solid or an intermediate state sample, such as a gel, can fill the entire sample space 32, or fill only a portion of the sample space 32. A solid or a gel sample 34 can be surrounded by a bath fluid. The attenuated total reflection technique need not be used with an optical cell according to the present invention.

The incident light beam is preferably directed to impinge on the sample in the sample space without being reflected by the back plate or by the spacer before impinging on the sample. The incident light beam is preferably directed so that light transmitted through, reflected by, or emitted by the sample is reflected at most once by the back plate or by the spacer while traveling through the sample.

The optical cell can be operated, for example, in a sample reflection mode, a back plate reflection mode, an emission mode, or a transmission mode. When the optical cell is operated in sample reflection mode, the incident light beam 36 is directed to impinge on the sample such that light is reflected from the sample back through the first optical window of the front plate 1; the reflected light can be analyzed, for example, by obtaining the spectrum. In a sample reflection mode, the back plate 2 can be transparent, opaque and reflective, or opaque and nonreflective, i.e., the optical properties of the back plate 2 have little importance. Any one or any combination of a range of back plate materials can be used: examples of materials which are transparent are calcium fluoride, barium fluoride, magnesium fluoride, zinc selenide, germanium, fused silica, borosilicate glass, quartz, or sapphire; examples of reflective opaque materials are steel, aluminum, copper, brass, silver, zinc, silver coated metal, gold coated metal, coated and uncoated metal, and coated and uncoated metal alloy.

In a back plate reflection mode, the incident light beam 36 is directed to impinge on the sample 34. Light travels through the sample and is reflected from the back plate 2. After reflection from the back plate 2, the light can travel again through the sample and then out of the first optical window of the front plate 1, or the light can travel from the back plate 2 through the sample space 32 but not through the sample and out of the first optical window of the front plate 1. After passing from the sample or the sample space 32 again through the first optical window of the front plate 1, the light can be analyzed, for example, by obtaining the spectrum. In this back plate reflection mode, the back plate 2 must be reflective. Any one or any combination of a range of reflective back plate materials can be used, for example, steel, aluminum, copper, brass, silver, zinc, silver coated metal, gold coated metal, coated and uncoated metal, and coated and uncoated metal alloy; materials that are transparent, but reflect a large percentage of light can also be used.

The optical cell can be operated, for example, in an emission mode. Modes of emission include spontaneous emission and induced emission. Examples of spontaneous emission include thermal emission, i.e., the emission of light associated with the temperature of the sample, and chemiluminescence, i.e., the emission of light as a product of a chemical reaction. Examples of light emission induced by exposure to electromagnetic radiation are fluorescence and Raman scattering. Light emission can also be induced by forms of energy other than electromagnetic radiation, for example, an electric current can induce electroluminescence. Phosphorescence, in which the emission of light is initially induced by exposure of a sample to electromagnetic radiation, but persists after the source of the electromagnetic radiation can also be viewed as emission and can be studied using the optical cell.

As a person of ordinary skill would recognize, transmission mode is often a desirable approach for spectroscopy. In a transmission mode, the initial light segment 36 is directed to impinge on the sample, light travels through the sample, and light travels through the back plate 2 and then can be analyzed, for example, by obtaining the spectrum. For operation in transmission mode, the back plate 2 must be transparent. Any one or any combination of a range of transparent back plate materials can be used, for example, calcium fluoride, barium fluoride, magnesium fluoride, zinc selenide, germanium, fused silica, borosilicate glass, quartz, or sapphire.

The incident light beam can include light of a single wavelength, multiple wavelengths, or a continuous spectrum of wavelengths. For example, the incident light beam can include light of wavelength ranging from the mid-infrared to vacuum ultraviolet, such as from about 50 μm to about 0.1 μm. This band of wavelengths includes electromagnetic radiation often referred to as infrared, visible, and ultraviolet. The wavelength of the light in the incident light beam and/or the wavelength of the light transmitted through, reflected by, emitted by, or scattered by the sample can be considered in selecting the first optical window and a second optical window. The incident light beam can be used, for example, to perform infrared, visible, or ultraviolet spectroscopy or to perform Raman spectroscopy. For example, a magnesium fluoride window can transmit light in the range of from about 0.12 μm to about 7 μm, a calcium fluoride window can transmit light in the range of from about 0.15 μm to about 10 μm, and a zinc selenide window can transmit light in the range of from about 0.5 μm to about 22 μm.

Examples of other factors to be considered in selecting the windows include the chemical compatibility of the window with a bath fluid or sample in the sample space 32 and the temperature which the window can tolerate. For example zinc selenide can dissolve is solutions of less than pH about 3. Calcium fluoride is slightly soluble in water. The small amount of calcium ions that enter the water can distort the results in certain experiments, for example, in certain biological experiments. The calcium can also precipitate out of solution as an insoluble salt. Barium fluoride has a greater solubility in water than calcium fluoride.

The advantage that windows can be readily exchanged in the optical cell and the ability to choose from many windows allows a window to be chosen that is optimal for the experiment.

An incident light beam can be directed to impinge on a sample in the sample space without being reflected by a back plate or by a spacer before impinging on the sample with an optical cell according to the present invention. In an optical cell according to the present invention, an incident light beam can be directed so that light transmitted through, reflected by, emitted by, or scattered by the sample is reflected at most once by a back plate or by a spacer while traveling through the sample.

When subjected to an increase in temperature, materials generally expand in linear dimensions. The constant relating the fraction of linear expansion to a temperature change is often termed the coefficient of linear expansion.

The optical cell according to the present invention can be spectroscopically stable. For example, the front plate 1, a first optical window in or forming the front plate 1, the back plate 2, a second optical window in or forming the back plate 2, the spacer 4, and the frame can be selected to have a height dimension and coefficient of linear expansion so that the sample gap changes with temperature by no more than 5 nm per Kelvin temperature change of the sample space, preferable no more than 3 nm per Kelvin temperature change of the sample space, and more preferably no more than 1 nm per Kelvin temperature change of the sample space. The frame can include, for example, a holder 3, a compensating plate 9, a compression plate 12, a first outer gasket 25, and a second outer gasket 26.

An optical cell could be actively corrected, meaning a user or a computing machine measures a current, actual parameter, determines how much it deviates from a target parameter value, and directs a manual or automatic adjustment of the device to bring the actual parameter within a tolerance of the target parameter value. For example, a user makes an active correction when the user measures a distance between two components of a device, subtracts the measured distance from a known target distance, and adjusts a screw or changes the voltage applied to a piezoelectric element to adjust the distance between the two components to within a tolerance of the known target distance. However, no active correction is required to maintain a sample gap of an optical cell according to the present invention constant upon a change in temperature. Instead, the selection of the dimensions of components of the optical cell and of the materials of which the components are made ensures that the sample gap remains constant with changes in temperature. An optical cell according to the present invention is non-actively thermal-expansion-compensated.

An example of a non-limiting, hypothetical model of the change in sample gap with a change in temperature is represented by Equation (1) for an optical cell in which the front plate 1 is formed by a first optical window, and the compression plate 12 is formed of the same material or of a material having the same coefficient of linear expansion as the holder 3.

$$\Delta d_{sg}/\Delta T = \alpha_h(d_{ow}+d_{bp}+d_s+d_{cp}+d_{g1}+d_{g2})-(\alpha_{ow}d_{ow}+\alpha_{bp}d_{bp}+\alpha_{cp}d_{cp}+\alpha_{g1}d_{g1}+\alpha_{g2}d_{g2}) \qquad \text{Eq. (1)}$$

The change in size of the sample gap is represented by $\Delta d_{sg}$, and the change in temperature is represented by $\Delta T$. The thickness at an initial temperature and the coefficient of linear expansion of the first optical window are represented by $d_{ow}$ and $\alpha_{ow}$, respectively. The thickness at an initial temperature and the coefficient of linear expansion of the back plate are represented by $d_{bp}$ and $\alpha_{bp}$, respectively. The thickness at an initial temperature of the spacer is represented by $d_s$, respectively. The thickness at an initial temperature and the coefficient of linear expansion of the compensating plate 9 are represented by $d_{cp}$ and $\alpha_{cp}$, respectively. The thickness at an initial temperature and the coefficient of linear expansion of the first outer gasket are represented by $d_{g1}$ and $\alpha_{g1}$, respectively; the thickness at an initial temperature and the coefficient of linear expansion of the second outer gasket are represented by $d_{g2}$ and $\alpha_{g2}$, respectively. The coefficient of linear expansion of the holder is represented by $\alpha_h$. When the compression plate 12 and the holder 3 are formed of the same material or of materials having the same coefficient of linear expansion, the height of the holder 3 that is relevant to calculating the change in the sample gap is the sum of the thicknesses of the first optical window, the back plate 2, the spacer 4, the compensating plate 9, the first outer gasket 25, and the second outer gasket 26 contained within the holder 3. If the temperature changes from the initial temperature by $\Delta T$, this height of the holder changes by $\Delta T \alpha_h(d_{ow}+d_{bp}+d_s+d_{cp}+d_{g1}+d_{g2})$. If the thicknesses of the first outer window, the back plate, the compensating plate, and the first and second outer gaskets did not change, and the spacer were somewhat compressed before the change in temperature, the sample gap would change by the same amount as the height of the holder changes. However, because these components have a non-zero coefficient of linear expansion, these thicknesses will change, and thus tend to reduce the effect of the change in the relevant height of the holder on the sample gap. The sum of the change in thicknesses from an initial summed thickness of these components upon a change from an initial temperature of $\Delta T$ is $\Delta T(\alpha_{ow}d_{ow}+\alpha_{bp}d_{bp}+\alpha_{cp}d_{cp}+\alpha_{g1}d_{g1}+\alpha_{g2}d_{g2})$. Thus, the change from the initial sample gap, $\Delta d_{sg}$, can be represented by Equation (1). When the thicknesses and coefficients of linear expansion of the component are selected so that the first group and the second group of terms on the right hand side of Eq. (1) are equal, the change from an initial sample gap symbolized by $\Delta d_{sg}$ can be zero even with a non-zero change in temperature $\Delta T$.

If the thickness of a component, such as the first optical window, is changed or the material from which a component is formed is changed, the thickness of the compensating plate 9 can be easily changed through machining, or another compensating plate of a different material with a different coefficient of linear expansion can be produced, to ensure that the first group and the second group of terms on the left hand side of Eq. 1 are equal or nearly equal. Because the design of the compensating plate 9 can be simple, a compensating plate 9 can be easily and inexpensively produced for each first optical window or each pair of first and second optical windows used with the cell. Most often, the initial sample gap, $d_s$, will be much smaller than the thickness of the first optical window, back plate, compensating plate, first outer gasket, or second outer gasket, symbolized by $d_{ow}$, $d_{bp}$, $d_{cp}$, $d_{g1}$, $d_{g2}$, respectively, so that a compensating plate 9 need not be remachined and a new compensating plate need not be produced when the sample gap changes. An advantageous, useful, and unexpected aspect of an optical cell according to the present invention is that the sample gap can be set, and the variation of the sample gap with temperature eliminated or controlled by the components surrounding the spacer 4, for example, the first optical window, back plate 2, first 25 and second 26 outer gaskets, compensating plate, and holder 3, rather than by the spacer 4 itself. For example, because the sample gap can be set by components other than the spacer 4, the thickness of a compressible spacer before placement in the optical cell can be larger than the target sample gap. Thus, it is not necessary to use expensive and complex techniques to produce a very thin spacer of uniform thickness in order to achieve a small sample gap.

When a spectrum is measured in a transmission mode, and the refractive indices of the first and the second optical windows are different from the refractive index of a liquid sample or of a bath fluid in the sample space 32, then some light is reflected at the interface of the second optical window and the sample space 32, and is again reflected at the interface of the first optical window and the sample space 32; a portion of this reflected light then travels through the second optical window where it contributes to the measurement of the spectrum of the liquid sample. The light reflected from the second and the first optical windows before traveling through the second optical window can interfere with the light passing directly through the sample space 32 and out of the second optical window. The constructive and destructive interference is thought to result in artifactual peaks and valleys of the spectrum, which are not representative of the true spectrum of the liquid sample. When the spectrum is measured in a back plate reflection mode, interference between light reflected from the back plate and passing back through the first optical window and light reflected from the back plate and then reflected from the first optical window and the back plate again before passing through the first optical window can occur. Constructive and destructive interference can occur in a measurement on a solid sample performed in a transmission or in a reflection mode.

If the spectrum of a first liquid sample is measured and the front plate 1, spacer 4, and back plate 2 are then disassembled to replace the first liquid sample with a second liquid sample on which a spectrum measurement is performed, the sample gap during the second measurement is likely to be different from the sample gap during the first measurement. Because the sample gap is different in the first and second measurements, the artifactual peaks and valleys resulting from constructive and destructive interference in the first and second spectra obtained will be different. Similarly, if the expansion of components in the cell with a change in temperature is not compensated for, so that the sample gap does not remain constant upon a change of temperature, then the spectrum of a sample measured at a first temperature will have different artifactual peaks and valleys resulting from interference than the spectrum of the sample measured at a second, higher temperature. A difference in the artifactual peaks and valleys in the spectrum obtained from a first measurement and in the spectrum obtained from a second measurement can render comparison of the spectrum associated with the sample in the first measurement and in the second measurement difficult. For example, comparison of the spectra can be facilitated by subtracting the spectrum of the first measurement from the spectrum of the second measurement. If the sample gap and the refractive index of the sample remain about the same between the first and the second measurement, the artifactual peaks and valleys introduced by interference into the first and second spectra will be about the same, and these artifactual peaks and valleys will be nulled in the difference spectrum. Thus, the difference spectrum will be substantially representative of the difference between the actual spectrum of the sample in the first measurement and the actual spectrum of the sample in the second measurement. If the sample gap changes between the first and the second measurements, the form of the artifactual peaks and valleys will change between the first and second measurements and will not be nulled in the difference spectrum; the presence of the artifactual peaks and valleys in the difference spectrum can obscure or confuse interpretation of the actual change in the spectrum of the sample in the first measurement and of the sample in the second measurement.

In an optical cell according to the present invention, the front plate 1 can contain one or more fluid inlets 6; the back plate 2 can contain one or more fluid inlets 6. A fluid tube 5 can be inserted in each fluid inlet 6. A fluid can be flowed from an environment through a fluid tube 5 and through a fluid inlet 6 into the sample space 32. A fluid can be withdrawn from the sample space 32 through a fluid inlet 6 and a fluid tube 5 into the environment. In an experiment, the front plate 1, spacer 4, and back plate 2 can be assembled to enclose an empty sample space 32; a liquid sample can be flowed through the fluid tube 5 and the fluid inlet 6 into the sample space 32. Similarly, a second liquid sample can be flowed into a sample space 32 to displace a first liquid sample without disassembling the front plate 1, spacer 4, and back plate 2 with which a spectrum of the first liquid sample in the sample space 32 was measured. Because the front plate 1, spacer 4, and back plate 2 need not be assembled in the course of measuring the spectrum of the first liquid sample and of measuring the second liquid sample, the sample gap during the measurement of the second liquid sample will be identical or very close to the sample gap during the measurement of the first liquid sample. Therefore, if the refractive indices of the first and the second liquid samples are similar, the artifactual peaks and valleys resulting from constructive and destructive interference are similar in the spectra obtained from the first and from the second measurement. The artifactual peaks and valleys can be nulled in a difference spectrum obtained from the first and second spectra, facilitating identification of the actual change in spectra of the first liquid sample and of the second liquid sample.

The front plate 1, the spacer 4, and the back plate 2 can be assembled with a solid sample in the sample space 32. For a first measurement, a first bath fluid can be flowed through a fluid inlet 6 and into the sample space 32 where the first bath fluid surrounds the sample. A first spectrum of the sample in the first bath fluid can be obtained. A second bath fluid can be flowed through a fluid inlet 6 and into the sample space 32; the displaced first bath fluid can flow through another fluid inlet 6 and out of the sample space 32. A second spectrum of the sample in the second bath fluid can be obtained. Because the cell has not been disassembled and reassembled, the sample gap remains constant, and the artifactual peaks and valleys resulting from constructive and destructive interference null out in the difference spectrum calculated from the first and second spectrum.

Because the optical cell according to the present invention has non-active compensation for dimensional changes in components induced by a change in temperature, the sample gap does not vary or varies only by a small percentage with a change in temperature. A first spectrum of a sample at a first temperature can be measured and a second spectrum of a sample at a second temperature can be measured. The form of the interference induced artifactual peaks and valleys in the first spectrum will be similar to the form of the interference induced artifactual peaks and valleys in the second spectrum. The artifactual peaks and valleys can be nulled out in the difference spectrum, so that the actual change in the spectrum of the sample at the first temperature and in the spectrum of the sample at the second temperature can be identified.

Maintaining a constant sample gap can be important when the response of the light detector in a microscope spectrometer used with an optical cell is nonlinear. For example, a detector can be nonlinear in that the output current or voltage varies nonlinearly with the intensity of light impinging on the detector. A detector can also be nonlinear in that the relationship between the intensity of impinging light and output current or voltage varies with the wavelength of the impinging light. Infrared detectors can exhibit both types of nonlinearity. If the sample gap changes with time, so that the thickness of a sample and/or surrounding bath fluid changes, the absorption of light at various wavelengths will change. When the detector is nonlinear, the spectrum will not change with a uniform scale factor at all wavelengths, rather, the fractional change of a given peak can depend both on the amplitude of absorbance and the wavelength of the peak. Thus, if the sample gap changes, the spectrum can appear qualitatively different.

Sample—time and bath fluid—time ramp experiments can be conducted with the optical cell according to the present invention. In a sample—time experiment, for example, the spectrum of a first liquid component, the spectrum of a second liquid component, and the spectrum of solutions of the first and second liquid components at various miscible proportions of the components can be obtained. The spectrum of a sample liquid can be continuously obtained over a period of time during which the sample liquid is initially composed of only the first component, and then over time the proportion of the second component in the first component is continuously increased, and finally the sample liquid is compose only of the second component. Because the front plate 1, spacer 4, and back plate 2 are not disassembled, the sample gap does not change, and artifactual peaks and valleys introduced by interference can be nulled out in a difference spectrum obtained from spectra measured for different proportions of the components in the sample liquid. A similar experiment could be performed where one component is a liquid and the second component is a solid that dissolves in the liquid, although the ramp of component proportions would end at the solubility limit of the solid in the liquid.

In an example of a bath fluid—time ramp experiment, a solid sample is placed into the sample space 32, and bath fluid is flowed into the sample space 32 through a fluid inlet 6, around the solid sample, and out of another fluid inlet 6. The spectrum of the solid sample can be continuously measured over a period of time, during which the proportion of components of the bath fluid are varied. The sample gap remains constant with time, so that artifactual peaks and valleys arising from interference can be nulled out in difference spectra. Furthermore, the same solid sample remains in the same position over the course of the experiment. A solid sample may have an irregular surface or may be non-homogeneous, and replacing the solid sample in the sample space 32 would probably change its orientation with respect to the incident light beam, so that the solid sample alone would have a different spectrum after replacement. Because the solid sample need not be replaced in the sample space 32 when the bath fluid is changed in the optical cell according to present invention, comparison of the spectrum of the sample with different bath fluid compositions is facilitated. Because the proportions of components of a liquid sample or a bath fluid can be continually and/or continuously varied with an optical cell of the present invention, data for sample—time and bath fluid—time ramp experiments can be obtained much more rapidly than if it were necessary to disassemble the cell.

Temperature ramp experiments can be conducted with the optical cell according to the present invention. The temperature of a liquid or solid sample in the sample space 32 can be continuously adjusted with the heater/cooler. Because of the non-active thermo-mechanical compensation of the cell, the percentage variation of the sample gap over a large temperature range is small, so that artifactual peaks and valleys resulting from light interference can be nulled in difference spectra obtained at two different temperatures.

Grooves 7 in the front plate 1 or in the back plate 2 can promote the flow of fluid around the sample. Grooves 7 can promote the rapid exchange of fluid in the sample space 32 when, for example, a first bath fluid is replaced by a second bath fluid or a first liquid sample is replaced by a second liquid sample. As another example, grooves 7 can promote the rapid exchange of fluid during a sample—time or a bath fluid—time ramp experiment. The grooves 7 can help prevent the formation of stagnant pockets or recirculations separated from the flow of fluid through the cell. Such stagnant pockets or recirculations can be problematic if, for example, the fluid flowing through the sample space 32 is changed, the fluid in the stagnant pockets or recirculations is not changed, but fluid in the stagnant pockets or recirculations diffuses into the flow through the sample space 32 over time.

The optical cell according to the present invention can be used in kinetics experiments. The sample space 32 has a small volume, and fluid can be flowed through the sample space 32, thus, a first liquid in the sample space can be rapidly exchanged with a second liquid. For example, a solid sample can be studied in which the sample reacts in a first manner with respect to a first liquid, but reacts in second manner with a second liquid. For example, the surface of the sample can bond at sites with a first set of molecules in the first liquid, and bond at the same sites with a second set of molecules in the second liquid, so that it is of interest to determine the rate at which the second set of molecules displace the first set of molecules at the sites when the first liquid is replaced by the second liquid. The spectrum of the solid sample, for example, the spectrum of light reflected by the surface of the solid sample, can be continuously measured over the period when the solid sample is surrounded by the first liquid, while the first liquid is being displaced by the second liquid, and when the solid sample is surrounded by the second liquid.

With an optical cell according to the present invention, a first liquid in the sample space 32 was found to be exchanged with a second liquid in the sample space within less than about 0.1 seconds. In the optical cell used, the back plate 2 had two grooves, each of approximate dimension of 0.5 mm depth, 0.5 mm width, and 5 mm length. The grooves were parallel to each other and separated by a distance of about 0.4 mm. A spacer of vacuum grease was used; the spacer occupied the outer regions of the surfaces of the front and back plate so that the region in, above, and between the grooves was unoccupied by spacer and available to be filled with sample. The sample gap in the region between the grooves and between the back plate 2 and the front plate 1 was 5 μm. Thus, the volume of the sample space was approximately 2.5 μL (microliters). The sample space was filled with a first fluid. As the spectroscope continually took measurements, a second fluid was injected into the sample space through a fluid inlet 6 at a flow rate of about 100 μL/s. From the spectroscopic measurements, about 90% of the first fluid was found to be displaced by the second fluid in 0.2 s or less; the spectroscope used to perform the measurement obtained a spectrum every 0.2 s. A model of the sample space as a continuous stirred tank reactor predicted that 90% of the first fluid is displaced by the second fluid in 0.06 seconds. Thus, an optical cell according to the present invention can be used to resolve reactions or mechanisms with time scales on the order of less than about 0.1 seconds.

An optical cell according to the present invention can be designed to allow even faster exchange of fluids. It is expected that proper selection of the sample gap, groove dimensions, and spacer dimensions can allow fluid to be exchanged in 1 millisecond. Thus an optical cell according to the present invention could be suitable for stopped flow experiments.

The optical cell can be used to study kinetics processes in liquids as well as in or on solids. For example, the optical cell can be used in reaction kinetics experiments in which a reaction, the cessation of a reaction, or a change in reaction kinetics is induced by a temperature change.

The temperature of the holder 3 can be measured with the temperature probe 13 inserted into the probe bore 40. A thermocouple or a resistance temperature detector can be used and coupled to a readout or coupled to an analog-to-digital converter in a computer to allow for automatic acquisition of temperature data. The temperature measured by the temperature probe 13 in the probe bore 40 is a close approximation to the temperature in the sample space 32. The holder and the compensating plate can be formed out of metal with a high thermal conductivity, to reduce any difference in temperature between the sample space 32 and the probe bore 40, and to allow for fast heating or cooling.

A calibration can be performed to account for any difference in temperature between the sample space 32 and the probe bore 40. For example, an auxiliary temperature probe can be placed into contact with the front plate 1 or can be placed inside the sample space 32. Several different temperatures can be imposed by a heater/cooler. The temperature measured by the auxiliary temperature probe can be compared to the temperature measured by the temperature probe 13 at each of the several imposed temperatures, and a correction equation relating the temperature measured by the temperature probe 13 to the temperature in the sample space 32 can be developed. The optical cell can be thermostatted. For example, the output of a thermocouple or a resistance temperature detector functioning as the temperature probe 13 can be coupled to a thermostat, which then regulates the power sent to the heater/cooler. With the holder 3 connected to a Peltier plate 14 and heat sink 15 with circulating heat transfer fluid as the heater/cooler, the temperature in the sample space 32 can be maintained to within about 0.1° C.; the cell temperature can be increased by 50° C. in about 100 seconds. Two or more heater/coolers, e.g., Peltier plates 14, evenly placed around the perimeter of and in contact with the holder 3 can induce a more uniform temperature throughout the holder 3 than if only one heater/cooler placed at one position on the holder 3 is used. In an embodiment, in which two Peltier plates 14 contact the holder, and a heat sink 15 with circulating heat transfer fluid is in contact with each Peltier plate, temperatures within the sample space 32 of from about −10° C. to about 100° C. can be achieved. For biological experiments, temperatures in a range of from about 5° C. to about 60° C. are often useful. For investigation of physical or chemical phenomena, a wide range of temperatures may be required; a heater/cooler configuration can be selected to achieve high or low temperatures.

The reference window 23 can be used to account for absorption of light by the first and second optical windows. For use in sample reflection mode and back plate reflection mode, the reference window 23 is formed of the same material as the first optical window and has the same thickness as the first optical window. In an embodiment, the reference receptacle 22 has dimensions such that the surface of reference window which faces away from the mounting plate 18 is at the same height as the surface of the first optical window which faces away from the mounting plate 18; before or after measuring the spectrum of a sample, the mounting plate 18 can be translated so that a spectral measurement can be taken through the reference window. In another embodiment, the incident light beam is split so that spectral measurement can be simultaneously taken of the sample in the sample space 32 and of the reference window 23. The measurement of the spectrum of the window can be used to correct the measured sample spectrum. For use in transmission mode, if the first and the second optical windows are formed of the same material, the reference window 23 can be formed of this material with a thickness equal to the combined thicknesses of the first and the second optical windows. If the first and the second optical windows are formed of different materials, the reference window can be formed of two pieces. The first piece can be of the same material and have the same thickness as the first optical window; the second piece can be of the same material and have the same thickness as the second optical window. A surface of the first piece and a surface of the second piece can be ground very flat, and these very surfaces placed into close contact so that there are essentially no reflection losses at the interface between the first and the second pieces. Alternatively, reference window can be made out of two pieces, and a potassium bromide crystal can be placed between the windows. The reference window can be mounted in a well near to the first and second optical windows in the holder. Independent of whether the reference window 23 is formed of a single piece or of two pieces, the reference receptacle 22 can have dimensions such that the surface of the reference window 23 which faces away from the mounting plate 18 is at the same height as the surface of the first optical window which faces away from the mounting plate 18.

In an embodiment, an incident light beam from a spectrometer passes through the atmosphere before entering the first optical window and the sample space 32. A spectroscopic measurement can, for example, be performed with an incident light beam having infrared wavelengths. Water vapor in the air can absorb a large fraction of infrared light in certain infrared wavenumber bands, especially if the beam path through the atmosphere is extended. If the light exiting the sample which will be spectroscopically analyzed travels through the atmosphere, additional infrared light can be absorbed by water vapor in the air. To reduce the effect of absorption of infrared light by the water vapor on the measured spectrum, the space in the environment between the exit of the incident light beam from the spectrometer and the first optical window can be shrouded to separate the rest of the atmosphere from the space inside the shroud. If a transmission mode spectrum is obtained, the space in the environment between where the light exits the second optical window and the light enters the spectrometer can also be shrouded. For example, a polyethylene sheet or other polymer film can be used as a shroud. To reduce the water vapor within the shroud, for example, water absorbing material, i.e., desiccant, can be placed inside the shroud or shrouds, or dry air can be continuously flowed into the shroud or shrouds. Preferably, nitrogen is flowed into the shroud or shrouds; as well as purging water vapor, the flowing nitrogen can purge carbon dioxide, which can absorb infrared radiation at wavelengths close to wavelengths absorbed by certain samples.

An optical cell according to the present invention can be mounted in a microscope spectrometer, for example, in an infrared microscope spectrometer. A microscope spectrometer can direct an incident light beam so that a light spot of small area impinges on the sample. A characteristic width can be used to describe the size of a light spot; for example, the characteristic width of a circular light spot is its diameter, the characteristic width of a square light spot can be the length of its diameter. For example, an infrared microscope spectrometer directing light of 5 μm wavelength can direct a light spot of 5 μm characteristic width to impinge on the sample. Certain spectrometers can, for example, direct a light spot of 5 μm wavelength and 2 μm characteristic width to impinge on a sample. To obtain a quantitative measurement of the spectrum of a sample, the sample should have an area such that the entire incident light beam falls onto the sample. For example, none of the incident light beam should pass through a bath fluid without passing through the sample. Because the optical cell according to the present invention can be mounted in a microscope so that the incident light beam can be focused to a small area on the sample, a small sample. For example, a small solid sample can be studied. Thus, with a microscope spectrometer capable of directing a light spot of characteristic width of 2 μm to impinge on a sample, a quantitative spectrum of a sample of characteristic width of 2 μm can be obtained. Certain microscope spectrometers use a focal array and are capable of resolving areas smaller than the area of the light spot at the position of the sample. For example, a microscope spectrometer can resolve an area of characteristic width of 1.3 μm when an incident light beam of 5 μm wavelength is used. In Raman spectroscopy, the Raman spectrum of an area of the sample of characteristic width of 0.5 μm can be resolved when an incident light beam of 1 μm wavelength is used. The optical device according to the present invention can accept samples ranging from macroscopic size, for example, about 10 mm, to less than about 1 μm in the sample space 32. By contrast, in a non-microscope spectrometer, for example, a non-microscope infrared spectrometer, an incident light beam is focused to a larger area, e.g., a spot of 1 mm diameter or greater, so that a large sample is required. When the optical cell of according to the present invention is mounted in a microscope spectrometer, the position of the sample space with respect to the microscope spectrometer can change with a change of temperature; however, this can be easily corrected for by adjusting the focus of the microscope spectrometer.

Experimental

There are several advantages associated with being able to obtain accurate spectroscopic information on small samples with an optical cell according to the present invention. For example, only a small sample may be available or the sample material may be very expensive. The sample itself may be large, but the area of interest may be small. The ability to obtain spectroscopic information on small areas of a samples allows features and structures at small length scales to be investigated. Spectroscopic measurements of small areas arrayed over the sample can be used to compose a spectroscopic map, such a map can be superposed on, for example, a visible light image. Such a map can be useful for looking at variation of, for example, concentration in, e.g., a diffusion experiment, dissociation constants, or number of binding sites over a sample. Such a map can also be developed using a microscope spectrometer with a focal array. In studying solid or gel samples in a bath fluid, it can be important for the distribution of absorbed bath fluid in the sample to reach equilibrium before a spectroscopic measurement is performed. The time for penetration of a liquid or gas substance into a sample varies approximately with the square of the distance into the sample.

For example, in an experiment, a sample of tendon of 100 μm width was immersed in light water ($H_2O$) in the sample space 32 of an optical cell according to the present invention. The light water was exchanged with heavy water (deuterium oxide). From spectroscopic measurements, it was found that the heavy water penetrated the tendon in about 30 s. If the tendon had been of 1 mm width, it is understood that the penetration time would have been 100 times as long, about 50 minutes. Thus, the ability of the optical cell according to the present invention to perform measurements on small samples allows spectra on a large number solid sample in a bath fluid to be obtained within a given period, and allows spectra of a single solid sample to be obtained with a large number of different bath fluids during a given period. Reaction kinetics of a small solid sample in a bath fluid can be spectroscopically observed at shorter timescales than reaction kinetics in a larger sample. A small area of sample can readily be made of uniform thickness. By contrast, a large area of sample is difficult to make of uniform thickness. A lack of uniform thickness across the spot of the incident light beam on the sample in conjunction with nonlinear behavior of a detector can result in artifacts in the spectrum.

As an example of spectroscopic stability, in an embodiment of the optical cell according to the present invention, the sample gap was found to be stable to within 3 nm over a two week period when the temperature in the sample space 32 was maintained constant. The observations were made with an optical cell in which the holder 3 and the compression plate 12 were made of red brass. The measurements were made in transmission mode, and the first and second optical windows each had a thickness of 2 mm. The compensating plates 9 used had a thickness of 4 mm, the holder 3 had a thickness of 13.6 mm, and the compression plate had a thickness at the edge of 4 mm and a thickness in the center region of 1.9 mm. In one pair of experiments, a sample of water was present in the sample space 32. A first measurement was conducted with first and second optical windows of calcium fluoride, a compensating plate 9 of red brass, and a sample gap of 5 µm. A peak in the water spectrum with an absorbance of 0.5 absorbance units was found to be stable within $10^{-4}$ absorbance units over two weeks. In fact, the infrared microscope spectrometer itself was only stable to within about $10^{-4}$ absorbance units over two weeks; thus, the optical cell may have exhibited a stability better than $10^{-4}$ absorbance units. A second measurement was conducted with first and second optical windows of zinc selenide, a compensating plate 9 of zinc, and a sample gap of 5 µm; a peak in the water spectrum with an absorbance of 0.5 absorbance units was found to be stable within $10^{-4}$ absorbance units over two weeks. Again, the infrared microscope spectrometer itself was only stable to within about $10^{-4}$ absorbance units over two weeks; thus, the optical cell may have exhibited a stability better than $10^{-4}$ absorbance units.

In another pair of experiments, a tendon sample was present in the sample space 32. A first measurement was conducted with first and second optical windows of calcium fluoride, a compensating plate 9 of red brass, and a sample gap of 5 µm; a peak in the tendon spectrum with an absorbance of 0.5 absorbance units was found to be stable within 10–4 absorbance units over two weeks. A second measurement was conducted with first and second optical windows of zinc selenide, a compensating plate 9 of zinc, and a sample gap of 5 µm. A peak in the tendon spectrum with an absorbance of from about 0.01 to about 1 absorbance unit was found to be stable within 10–4 absorbance units over two weeks. Stability of the peaks within 10–4 absorbance units indicated that any change in the sample gap over two weeks was less than 3 nm. The optical cells were spectroscopically stable.

The spectroscopic stability of an optical cell according to the present invention can be assessed, for example, by evaluating the stability of the sample gap. The stability of the sample gap in an optical cell according to the present invention with varying temperature was determined through experiment. In a first test the sample space 32 contained air. A light beam was directed into the cell, and the sample gap at the center of the sample space was measured by observing the wavenumber of peaks, i.e., maxima, and valleys, i.e., minima, in the spectrum of the reflected light. The peaks and valleys resulted from constructive and destructive interference of the light traveling from the interface of the first optical window 1 through the sample space 32 to the back plate 2 and the light reflected from the back plate 2 and traveling back through the sample space 32 towards the first optical window 1. The distance of a sample gap was determined to within an accuracy of ±50 nm. Some of the uncertainty in measurement can be attributed to systematic error, therefore, the difference between a sample gap measured at a first temperature and a sample gap measured at a second temperature without disassembling the optical cell or separating the front plate 1 or the back plate 2 from the spacer 4 was determined to within an accuracy of ±20 nm. The sample gap was measured at temperatures of 10, 20, 30, and 45° C. The largest sample gap of 4.84 µm was measured at 30° C., and the smallest sample gap of 4.81 µm was measured at 45° C. Intermediate values of the sample gap were measured at 10° C. and 20° C. Thus, the sample gap changed by a maximum of 30 nm across the range of 10° C. to 45° C., equivalent to 0.64% of the sample gap, and an average of 0.9 nm/K and 0.018% of the sample gap per Kelvin over that range. The sample gap change over the interval from 30° C. to 45° C. was only an average of 2.1 nm/K and 0.04% of the sample gap per Kelvin over that range.

A second experiment was conducted with air in the sample space. The first and the second optical windows were made of calcium fluoride, the compensating plate 9 was made of red brass, and the holder 3 and compression plate 12 were made of red brass. A sample gap of 0.72 µm was measured at 5° C., a sample gap of 0.71 µm was measured at 25° C., and a sample gap of 0.69 µm was measured at 50° C. Thus, the sample gap changed by 25 nm over range from 5° C. to 50° C., equivalent to 3.6% of the sample gap, an average of 0.6 nm/K and 0.08% of the sample gap per Kelvin over that range.

For a third experiment, the first and the second optical windows were made of calcium fluoride, the compensating plate 9 was made of red brass, and the holder 3 and compression plate 12 were made of red brass. A sample of dried tendon was present in the sample space 32. The dried tendon had a refractive index similar to that of the windows, so that light did not substantially reflect at the tendon—window interfaces, constructive and destructive interference of reflected and incident light did not substantially occur, and peaks and valleys in the spectrum could not be used to determine the sample gap at the center. Therefore, measurements of the sample gap were taken at several positions around the dried tendon and the sample gap at the center of the cell was interpolated from these measurements for each temperature investigated. Interpolated sample gaps of 7.95 µm at 5° C., 7.99 µm at 20° C., 8.01 µm at 35° C., 8.01 µm at 50° C., and 7.94 µm at 80° C. were determined. Thus, the largest sample gap was determined at 35° C., and the smallest sample gap was determined at 80° C. The sample gap changed by a maximum of 74 nm across the range of 5° C. to 80° C., equivalent to 0.93% of the sample gap, and an average of 0.99 nm/K and 0.012% of the sample gap per Kelvin over that range. The sample gap changed by 36 nm over the interval from 5° C. to 20° C., equivalent to 0.45% of the sample gap, and an average of 2.4 nm/K and 0.03% of the sample gap per Kelvin over that range. The sample gap changed by 72 nm over the interval from 50° C. to 80° C., equivalent to 0.90% of the sample gap, and an average of 2.4 nm/K and 0.03% of the sample gap per Kelvin over that range.

Over a given range of change in temperature, the sample gap variation with temperature is less than about 5 nm/K.

Preferably, the sample gap variation is less than about 3 nm/K, and most preferably the sample gap variation is less than about 1 nm/K.

For an optical cell according to the present invention, the sample gap is expected to change by no more than 160 nm with a change in temperature of 50 K. The sample gap can change by less than or equal to about 80 nm with a change in temperature of 50 K. The sample gap can change by less than or equal to about 10 nm with a change in temperature of 50 K. Thus, under normal room temperature conditions ranging from 20 to 30 degrees, the sample gap will not vary more than about 5 nm, 10 nm, 20 nm, 30 nm, 50 nm, 60 nm, or 100 nm in embodiments of the invention.

The spectroscopic stability of an optical cell of the present invention can be assessed, for example, by evaluating the ability to detect a trace component in a solution from spectroscopic measurements of the solution and of the solvent in the solution. When light passes through a material which absorbs the light, the intensity of the light decreases exponentially with the distance through which it has passed in the material. It is common to represent the absorption of light in spectroscopic measurements as absorbance units. The absorption of light in absorbance units is equal to the negative of the base 10 logarithm of the quotient of the intensity of the light incident on a material divided by the intensity of the light that has passed through the material. For example, a sample with an absorbance of 1 absorbance unit has transmitted 10% of the incident light and has absorbed or scattered 90% of the incident light. Of the light that has not been transmitted through the sample, some may have been scattered rather than absorbed by the sample; however, in this text, the term absorbed light refers to light that has not been transmitted.

The ability of a spectroscopy system using an optical cell according to the present invention to detect a trace amount of a component in a solvent was determined through experiment. The optical cell used in the experiment was constructed as follows. The holder 3 had a thickness of 13.6 mm, the compression plate 12 had a thickness at the edge of 4 mm and in the center region of 1.9 mm, and the compensating plate 9 had a thickness of 4 mm; these parts were constructed of red brass. The front plate 1 was formed entirely of the first optical window, and the back plate 2 was formed entirely of the second optical window. The first and the second optical windows were 2 mm thick and 13 mm in diameter and were constructed of calcium fluoride. The second optical window had two grooves of approximate dimensions 0.5 mm depth, 0.5 mm width, and 5 mm length; the grooves were parallel and separated by 0.4 mm. The first outer gasket and the second outer gasket were constructed of three to four layers of aluminum foil. The spacer which separated the first optical window and the second optical window was formed of a fluorinated silicone vacuum grease. The grease forming the spacer was applied to the outer regions of the surfaces of the first and second optical windows so that the region in, above, and between the grooves was unoccupied by spacer and available to be filled with sample. The thickness of the spacer was about 5 μm and the sample gap was about 5 μm.

The solvent, water, was placed into the sample space 32 of the optical cell, and the spectrum of the solvent was taken in transmission mode. The sample gap in the optical cell was 5 μm and the optical cell was thermostatted at 25.0±0.1° C. A solution of 0.005 vol % of the trace component, N-methyl-formamide, in the solvent, water, was made. After the solvent spectrum had been obtained, the solution was flowed into the sample space 32 through a fluid tube 5 and a fluid inlet 6 in the front plate 1. After the water had displaced essentially all of the solution, the spectrum of the solution was obtained in transmission mode. Because the front plate 1, the spacer 4, and the back plate 2 were not disassembled to introduce the solution into the sample space 32, the sample gap remained essentially the same as when the spectrum of the solvent, water had been obtained. The marker peak of the trace component, that is, the peak associated with and used to identify N-methyl-formamide, was at 1659 cm−1. The masking peak of the solvent, water, that is, the peak of the solvent that overlapped with the marker peak, was at 1644 cm−1. In the solution spectrum, the masking peak of the water obscured the marker peak of the solvent, N-methyl-formamide. In order to assess the accuracy with which a spectrum can be obtained with the device, the following approach was taken. The water spectrum was multiplied times the volume fraction of water in the solution to obtain a weighted solvent spectrum. In other words, the intensities in the solvent spectrum were scaled by the volume fraction of water. The weighted solvent spectrum is subtracted from the solution spectrum to obtain a difference spectrum; that is, the absorption in the weighted solvent spectrum at a given wavenumber is subtracted from the absorption in the solution spectrum at the same number for all wavenumbers in the spectra. The difference spectrum is representative of the contribution of the spectrum of the pure solvated trace component to the solution spectrum. In this experiment, the difference spectrum is representative of the water solvated N-methyl-formamide. In the experiment, the presence of the marker peak indicative of the presence of N-methyl-formamide in the solution was identified in the difference spectrum. The absorption of the marker peak of the N-methyl-formamide in the solution was $1.5 \times 10^{-4}$ absorption units at 1659 cm−1; the absorption of the masking peak of the water in the solution was about 0.5 absorption units at 1644 cm−1.

The spectroscopic stability of an optical cell according to the present invention can be assessed, for example, by determining the minimum change in a sample peak in absorbance units that can be detected with a spectroscopic measurement when using the optical cell. It is thought that upon changing a fluid in the sample space 32 of an optical cell according to the present invention, a change in infrared peak absorbance of $1 \times 10^{-4}$ absorbance units can be detected. By contrast, a prior art optical cell requires the cell to be disassembled and reassembled in order to change the fluid. This disassembly and reassembly is expected to result in a changed sample gap. An optical cell such as that of Kal'nin is expected to be able to accurately measure a change in infrared peak absorption of $5 \times 10^{-3}$ absorption units, i.e., 50 times less sensitive than an optical cell according to the present invention. With an optical cell of the present invention, it is thought that a change in infrared peak absorbance of a solid sample of about 10-4 absorbance units can accurately be detected. By contrast, commercial optical cells are thought to be able to allow accurate detection of changes in infrared peak absorbance of a solid sample of from about 0.01 absorbance units to about 0.1 absorbance units, that is, 100 to 1000 times less sensitive than an optical cell according to the present invention.

The spectroscopic stability of an optical cell can be assessed by, for example, measuring a first spectrum of a solid or intermediate state sample, determining the ratio of two peaks in the first spectrum, changing the bath liquid surrounding the sample for fresh bath liquid of the same chemistry, measuring a second spectrum of the sample, and comparing the ratio of the two peaks in the second spectrum with the ratio of the two peaks in the first spectrum. The bath liquid can be changed and the spectrum measured several times, so that a standard deviation of the ratios can be determined. For example, the bath liquid can be changed and the spectrum remeasured four times. It is estimated that in using a commercial cell in which the cell has to be disassembled to change the bath liquid, such as water, surrounding a gel sample, such as polyacrylamide, for two peaks having absorbance of from 0.3 to 1.5 absorbance units and lying within the range of 2000 cm−1 to 700 cm−1, the standard deviation of the ratio of the two peaks obtained from several measurements will be from about 3 to about 30%. By contrast, it is estimated that in using an optical cell according to the present invention, which does not need to be disassembled to change the bath liquid, the standard deviation of the peak ratio from several experiments, for example, 5 measurements, will be within 0.3%, and can be within 0.03%.

The spectroscopic stability of an optical cell according to the present invention can be assessed by, for example, evaluating the performance of an optical cell subjected to a change in temperature by, for example, measuring, in transmission mode, a first spectrum of water or of air present in a sample space at a first temperature, changing the temperature, and then measuring, in transmission mode, a second spectrum of the water or of the air, using optical windows having a refractive index of at least about 2. The first spectrum can be subtracted from the second spectrum to obtain a difference spectrum. Within a range of wavenumbers, the lowest absorption, i.e., the lowest valley, in the spectrum is subtracted from the highest absorption, i.e., the highest peak, to obtain a value, the difference spectrum variation. With the spectrum obtained at the lower of the two temperatures, with the same range of wavenumbers, the lowest valley is subtracted from the highest peak to obtain a low temperature spectrum variation. The difference spectrum variation is divided by the low temperature spectrum variation to obtain the normalized difference spectrum variation. For a water sample, the range of wavenumbers should be selected to avoid wavenumbers where water exhibits strong absorption. The normalized difference spectrum is representative of the change in the form of artifactual peaks resulting from interference of light passing directly through the first optical window, the sample space, and the second optical window with light additionally reflected by the second and the first optical windows one or multiple times before exiting through the second optical window upon a change in temperature. The change in the form of artifactual peaks can result from the change in sample gap associated with the expansion of components upon a change in temperature. The change in the form of artifactual peaks using a water sample can also be influenced by change in refractive index of the water with a change in temperature; however, the change in sample gap is expected to contribute more substantially to the change in the form of artifactual peaks than a change in water sample refractive index.

Performance of an optical cell in terms of the normalized difference spectrum variation has been estimated through calculation based on the change in the contribution to artifactual peaks by light interference associated with the expected change in sample gap upon a change in temperature and the refractive index of air or water.

Water: Hypothetical transmission mode measurements of the spectrum of a water sample at 10° C. and at 50° C., using first and second optical windows of refractive index greater than 2, such as zinc selenide windows, can be considered. Considering the range of wavenumbers from 4000 cm−1 to 7000 cm−1, for a 1 μm sample gap, a normalized difference spectrum variation of 0.05 was calculated for an optical cell according to the present invention. By contrast, for a standard commercially available cell, a normalized difference spectrum variation of 1.0 was calculated. Table 1 presents the calculated normalized difference spectrum variation for hypothetical measurements using an optical cell according to the present invention and using a commercially available optical cell with a water sample and a range of sample gaps. The calculated normalized difference spectrum variation for a commercial optical cell for sample gaps of 0.5 μm and 1 μm are set off in angular brackets because commercial optical cells typically cannot be used with sample gaps less than 5 μm.

TABLE 1

Water Sample

| Commercial Optical Cell | | Optical Cell According to Present Invention | |
|---|---|---|---|
| Sample Gap | Normalized Difference Spectrum Variation | Sample Gap | Normalized Difference Spectrum Variation |
| 0.5 μm | <0.4> | 0.5 μm | 0.05 |
| 1 μm | <1.0> | 1 μm | 0.05 |
| 5 μm | 2.0 | 5 μm | 0.25 |
| 15 μm | 2.0 | 15 μm | 0.8 |

Air: Calculations were performed using a range of wavenumbers from 4000 cm−1 to 7000 cm−1, with air in the sample space, assumed to have a refractive index of 1. For an optical cell according to the present invention and a sample gap of 1 μm, a normalized difference spectrum of 0.04 was calculated. By contrast, for a standard commercially available cell, a normalized difference spectrum of 0.8 was calculated. Table 2 presents the calculated normalized difference spectrum variation for hypothetical measurements using an optical cell according to the present invention and using a commercially available optical cell with an air in the sample space and a range of sample gaps.

TABLE 2

Air Sample

| Commercial Optical Cell | | Optical Cell According to Present Invention | |
|---|---|---|---|
| Sample Gap | Normalized Difference Spectrum Variation | Sample Gap | Normalized Difference Spectrum Variation |
| 0.5 μm | <0.5> | 0.5 μm | 0.02 |
| 1 μm | <0.8> | 1 μm | 0.04 |
| 5 μm | 2.0 | 5 μm | 0.23 |
| 15 μm | 2.0 | 15 μm | 0.65 |

An optical cell according to the present invention was used with infrared spectroscopy measurements in an experiment in which the number of binding sites on collagen for phosphate and sulfate anions was determined. The optical cell included two zinc selenide windows for the first optical window which formed the entire front plate 1 and for the second optical window which formed the entire back plate 2. Reference numbers are provided to correlate with the figures, for convenience. The first optical window and the second optical window were separated by a spacer 4: a layer of fluorinated silicone grease around the outer perimeter of the surfaces of the windows facing towards the sample space 32. The top window included two fluid inlets 6: one through which liquid was injected into the sample space 32 and one through which liquid was released from the sample space 32. The windows and spacer 4 were placed inside a holder 3, formed of red brass; a second outer gasket 26 separated the surface of the second optical window facing away from the sample space 32 from the holder 3. A first outer gasket 25 was in contact with the first optical window. A compensating plate 9 of zinc was in contact with the first outer gasket 26. A compression plate 12 of red brass was in contact with the holder 3 and the first outer gasket 25; the compression plate 12 was screwed into the holder 3 to apply a small pressure to the assembly of the compensating plate 9, the first outer gasket 25, the first optical window, the spacer 4, the second optical window, and the second outer gasket 26 in the holder to ensure that these components were in contact throughout the experiment. Sample gaps of from about 3 μm to about 10 μm were used in the experiments. The first outer gasket 25 was formed of 3 to 4 layers of aluminum foil, and the second outer gasket 26 was formed of 3 to 4 layers of aluminum foil. A resistance temperature device was used as the temperature probe 13, and was inserted into the probe bore 40 in the holder 3. The temperature of the sample space 32 was controlled to within 0.1° C. by Peltier plates mounted on the holder 13. A fiber from rat tail tendon was used as the sample; once the sample was sandwiched between the first optical window and the second optical window, the rat tail tendon was 5000 μm in length, from 50 μm to 150 μm in width, and from 3 μm to 10 μm in thickness. After placement in the sample space 32, the sample was washed with the bath fluid with which the spectrum would be measured; the sample was annealed by heating and then cooling the sample space 32 several times between the temperatures of 5° C. and 45° C. The variation of the absorbance of the sample peaks was less than 2×10-4 during an experiment. A Continuum infrared microscope from Thermo Nicolet Corp. of Madison, Wis. having a narrow-band MCT/A detector and a 15× Reflachromat IR objective/condenser was used in conjunction with a Nexus 670 FTIR (Fourier Transformed Infrared) spectrometer having a potassium bromide beamsplitter from Thermo Nicolet Corp. This infrared microscope spectrometer collected spectra in the range of from 700 cm−1 to 7000 cm−1. A spectrum was determined from 300 interferometer scans at 4 cm−1 resolution. Three to 10 spectra were averaged together to obtain a result spectrum. The infrared microscope spectrometer allowed the incident light beam to be continuously focused on a selected region of the fiber, and to have all of the incident light beam pass through the sample rather than the fiber obtaining accurate quantitative measurements. Changes in the spectrum caused by exchange of the bath fluid was found to typically occur within about 15 minutes for acid-treated tendon samples and within about 120 minutes for untreated tendon samples. Spectra were recorded and equilibration was complete and no further spectral changes were observed.

In a first calculation method, the volume fraction of interstitial water inside collagen fibrils, $\theta_{wc}$, plus the volume fraction of bulk water filling the voids between fibrils, $\theta_{wb}$, and other "defects" was determined for fully hydrated noncrystalline rat tail tendon fibers by comparing the measured spectrum of the sample in the range from 3000 to 3600 cm−1 with the reference spectrum of water. The volume fraction of collagen, $\theta_c$, was determined by subtracting the volume fraction of interstitial water inside collagen fibrils and the volume fraction of bulk water in voids and defects from unity, i.e., Eq. (2).

$$\theta_c = 1 - \theta_{wc} - \theta_{wb}$$ Eq. (2)

The approximate volume fraction of interstitial water inside collagen fibrils was determined by multiplying the volume fraction of collagen by a factor of 1.2, i.e., Eq. (3).

$$\theta_{wc} = 1.2\theta_c$$ Eq. (3)

The accuracy of this first calculation method was limited by the distortion of the infrared spectrum of the water due to the altered structure of the interstitial water inside collagen fibrils.

The volume fractions were determined in a second method by estimating $\theta_c$ as 0.45 for samples with a minimal amount of bulk water and calibrating the intensity of non-dichroic collagen absorption bands at 1082 cm−1 and 1033 cm−1. The intensities of these bands was used to determine the $\theta_c$ in other samples and to determine $\theta_{wc}$ and $\theta_{wb}$ from Eq. (2) and Eq. (3). For this second method, the assumption was made that the calibration samples contained no bulk water voids, yet were fully solvated. The volume fractions were determined in a third method by subtracting the scaled spectra of sample with no or a minimal amount of bulk water from the spectra of samples which had substantial voids with bulk water; the scaling was determined by matching the intensities of the 1082 cm−1 and 1033 cm−1 bands. The difference spectrum was thought to represent the bulk-like spectrum of water in the voids. The difference spectrum was compared with the spectrum of water to determine $\theta_{wb}$; the value of $\theta_{wb}$ was then used with Eq. (2) and Eq. (3) to determine $\theta_{wc}$ and $\theta_c$. The values obtained from all three methods were compared; from the comparisons, it was estimated that $\theta_c$ was determined within 10%, $\theta_{wc}$ was determined within 10%, and $\theta_{wb}$ was determined within 20% in samples with substantial voids and was poorly defined in samples containing a volume fraction of bulk water of less than 10%.

Tendon samples were prepared from 6 week old rat tails. Tendons were removed from the tail, and washed and stored in an aqueous solution of 3.5 M sodium chloride, 10 mM Tris, 20 mM EDTA, 2 mM NEM, and 1 mM PMSF at pH 7.5 and 4° C. Before measurement with the optical cell, the tendons were washed for a few hours in an aqueous solution of 20 mM sodium chloride and 10 mM HEPES at pH 7.5 and 25° C.

The spectrum of a fiber with no sulfate or phosphate ions was subtracted from the spectrum of fiber formed with a given concentration of sulfate ions in solution; the spectrum of a fiber with no sulfate or phosphate ions was scaled and subtracted from the spectrum of fiber formed with a given concentration of phosphate ions in solution. The 1104 cm−1 band for sulfate, the 987 cm−1 band for dibasic phosphate, and the 932 cm−1 band for monobasic phosphate in the difference spectra were used to determine concentrations of sulfate and phosphate ions inside collagen fibers. The concentration of sulfate and of phosphate ions bound to collagen, dissolved in the interstitial water in the collagen fibrils, and in the bulk water in voids between fibrils and in defects were understood to be proportional to the volume fractions of collagen, interstitial water, and bulk water. The concentration of sulfate or phosphate ions in the sample was plotted as a function of the concentration of sulfate or phosphate ions in the solution from which the fibers were assembled. From this data, the number of binding sites per collagen molecules, the dissociation constant, the apparent anion penetration coefficient, and the partition coefficient for interstitial water were calculated. The dissociation constant of dibasic phosphate was found to increase with pH. Increased concentration of sodium chloride in a certain range of concentration was found to increase the dissociation constant of sulfate and of dibasic phosphate. Under physiological conditions, dibasic phosphate and sulfate was found to bind at from 1 to 2 sites per collagen molecule. At pH 6.8, the dissociation constant for phosphate and for sulfate from sites on a collagen molecule was found to be about 2 mM. Thus, the optical cell is useful for measuring effects of intentional temperature change in aqueous media or for neutralizing effects of unintended temperature change.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. An optical cell, comprising:
a front plate having a first optical window through which an incident light beam can pass;
a back plate;
a spacer in contact with the front plate and the back plate, the spacer being separable from the front plate and the back plate;
the front and back plates and the spacer defining a sample space capable of containing a sample and having a sample gap between the front plate and the back plate;
a frame in contact with the front plate and with the back plate;
the front plate, back plate, spacer, and frame having coefficients of linear expansion and height dimensions so that the optical cell is spectroscopically stable with respect to varying temperature of the sample space in a temperature range of experimentation.

2. The optical cell of claim 1, wherein the volume of the sample space is less than or equal to about 20 microliters.

3. The optical cell of claim 1, wherein the volume of the sample space is less than or equal to about 5 microliters.

4. The optical cell of claim 1, wherein the smallest dimension of the sample space in a plane parallel to the first optical window is at least about five times the sample gap.

5. The optical cell of claim 1, wherein a sample that comprises a solid can be placed into and removed from the sample space.

6. The optical cell of claim 1, wherein the sample space may receive a liquid sample.

7. The optical cell of claim 1, further comprising at least one fluid inlet, wherein a liquid sample can flow through the fluid inlet, into the sample space, and out of the sample space.

8. The optical cell of claim 1, the front plate, back plate, spacer, and frame being selected to have coefficients of linear expansion and height dimensions so that the sample gap changes with temperature by no more than 5 nm per Kelvin temperature change of the sample space in a temperature range of spectroscopic measurement.

9. The optical cell of claim 1, the front plate, back plate, spacer, and frame being selected to have coefficients of linear expansion and height dimensions so that, without active correction, the sample gap changes with temperature by no more than 3 nm per Kelvin temperature change of the sample space in a temperature range of spectroscopic measurement.

10. The optical cell of claim 1, wherein the sample gap is in a range of from about 0.1 µm to about 3 µm.

11. The optical cell of claim 1, the frame comprising a holder, a compensating plate, and a compression plate.

12. The optical cell of claim 11,
wherein the holder, the compression plate, and the compensating plate each comprise a material selected from the group consisting of red brass, brass, copper, zinc, aluminum, steel, and alloys thereof.

13. The optical cell of claim 11, wherein the compression plate is formed of the same material as the holder.

14. The optical cell of claim 11, the frame further comprising a first outer gasket and a second outer gasket.

15. The optical cell of claim 14,
wherein the outer gaskets each comprise a material selected from the group consisting of aluminum, gold, silver, and copper.

16. The optical cell of claim 1, wherein when a polyacrylamide gel sample in a water bath liquid in the sample space has a measured peak in the spectrum with an absorbance from 0.3 to 1.5 absorbance units within the range of 2000 $cm^{-1}$ to 700 $cm^{-1}$, and the water bath liquid is exchanged with fresh water bath liquid and the spectrum is remeasured four additional times, the standard deviation of the absorbance of the measured peak will be within 0.3%.

17. The optical cell of claim 16, wherein the standard deviation of the absorbance of the measured peak will be within about 0.03%.

18. The optical cell of claim 1, the front plate, back plate, spacer, and frame being selected to have coefficients of linear expansion and height dimensions so that the difference between the maximum sample gap and the minimum sample gap is no greater than 80 nm during a temperature change of 50 K.

19. The optical cell of claim 1, the front plate, back plate, spacer, and frame being selected to have coefficients of linear expansion and height dimensions so that the difference between the maximum sample gap and the minimum sample gap is no greater than 10 nm during a temperature change of 50 K.

20. The optical cell of claim 1, the back plate having a second optical window.

21. The optical cell of claim 1, the front plate, back plate, spacer, and frame being selected to have coefficients of linear expansion and height dimensions so that when the first optical window is of zinc selenide, water is the sample, and the temperature in the sample space is maintained constant, for a peak at 1644 cm−1 in the water spectrum with an absorbance of 0.5 absorbance units, the absorbance of the peak remains stable within about $5\times10^{-4}$ absorbance units over two weeks.

22. The optical cell of claim 21, wherein the absorbance of the peak remains stable within about $1\times10^{-4}$ absorbance units over two weeks.

23. The optical cell of claim 1, wherein the spectrum of a solvent sample in the sample space is obtained, the spectrum of a solution including a trace component and the solvent is obtained, the trace component spectrum has a marker peak, the solvent spectrum has a masking peak which overlaps with the marker peak, a difference spectrum is obtained from subtraction of the solvent spectrum multiplied by the volume fraction of the solvent in the solution, the masking peak of the solvent in the spectrum of the solution is greater than or equal to about 0.3 absorbance units, and the intensity of the marker peak of the trace component in the difference spectrum is less than or equal to about $10^{-3}$ absorbance units.

24. The optical cell of claim 1, wherein when the back plate has a second optical window, the first optical window and the second optical window comprise calcium fluoride, the sample gap is about 5 µm, the sample space is maintained at about 25° C., the spectrum of a water sample in the sample space is measured in transmission mode, the spectrum of a sample of a solution of 0.005 vol % of N-methyl-formamide in water in the sample space is measured in transmission mode, the water spectrum is scaled by the volume fraction of water and the scaled spectrum is subtracted from the solution spectrum to obtain a difference spectrum, the determined absorption of the peak induced by N-methyl-formamide at 1659 cm$^{-1}$ is from about $1 \times 10^{-4}$ to about $2 \times 10^{-4}$ absorption units.

25. The optical cell of claim 1, wherein the first optical window comprises a material selected from the group consisting of calcium fluoride, magnesium fluoride, barium fluoride, zinc selenide, and diamond.

26. The optical cell of claim 1, the back plate comprising a second optical window, wherein the second optical window comprises a material selected from the group consisting of calcium fluoride, magnesium fluoride, barium fluoride, zinc selenide, and diamond.

27. The optical cell of claim 1, the back plate having a second optical window, wherein the first optical window and the second optical window comprise calcium fluoride.

28. The optical cell of claim 1, wherein the spacer comprises at least one of silicone vacuum grease, fluorinated silicone vacuum grease, polytetrafluoroethylene, polyethylene terephthalate, polyethylene, and polypropylene.

29. The optical cell of claim 1, further comprising a heating/cooling element.

30. The optical cell of claim 29, wherein the heating/cooling element includes a Peltier plate.

31. A spectroscopy system, comprising the optical cell of claim 1 and a spectrometer, which directs an incident light beam onto a sample contained within the sample space and receives a light transmitted, reflected, or emitted by the sample.

32. The spectroscopy system of claim 31, wherein a kinetic process occurring on or within the sample with a process time of less than or equal to about 0.2 seconds can be identified by the spectrometer.

33. The spectroscopy system of claim 31, wherein a kinetic process occurring on or within the sample with a process time of less than or equal to about 0.001 seconds can be identified by the spectrometer.

34. The optical cell of claim 1, wherein the front plate, back plate, and spacer are capable of containing a solid sample or a gel sample within the sample space.

35. The optical cell of claim 1, wherein the optical cell is mounted in a microscope mounting.

36. A method comprising placing a sample in an optical cell according to claim 1, directing an incident light beam at the sample, and measuring the spectrum of light transmitted through, reflected by, emitted by, or scattered by the sample.

37. The optical cell of claim 1, the front plate, back plate, spacer, and frame being selected to have coefficients of linear expansion and height dimensions so that the sample gap changes with temperature by no more than 5 nm per Kelvin temperature change of the sample space in a temperature range of experimentation.

38. The optical cell of claim 37,
wherein the front plate comprises an optical window,
wherein the frame comprises a compensating plate, a first outer gasket, a second outer gasket, and a holder,
the optical window having a coefficient of linear expansion $\alpha_{ow}$ and a height dimension $d_{ow}$, the back plate having a coefficient of linear expansion $\alpha_{bp}$ and a height dimension $d_{bp}$, the compensating plate having a coefficient of linear expansion $\alpha_{cp}$, and a height dimension $d_{cp}$, the first outer gasket having a coefficient of linear expansion $\alpha_{g1}$ and a height dimension $d_{g1}$, the second outer gasket having a coefficient of linear expansion $\alpha_{g2}$ and a height dimension $d_{g2}$, the spacer having a height dimension $d_s$, and the holder having a coefficient of linear expansion $\alpha_h$,
wherein upon a change of temperature $\Delta T$, the size of the sample gap changes as $\Delta T(\alpha_h(d_{ow}+d_{bp}+d_s+d_{cp}+d_{g1}+d_{g2})-(\alpha_{ow}d_{ow}+\alpha_{bp}d_{bp}+\alpha_{cp}d_{cp}+\alpha_{g1}d_{g1}+\alpha_{g2}d_{g2}))$,
and wherein upon a 1 Kelvin change of temperature, the sample gap changes by no more than 5 nm.

39. The optical cell of claim 1, the front plate, back plate, spacer, and frame being selected to have coefficients of linear expansion and height dimensions so that, without active correction, the sample gap changes with temperature by no more than 3 nm per Kelvin temperature change of the sample space in a temperature range of experimentation.

40. A method for obtaining an optical spectrum of a sample, comprising:
placing the sample in a sample space of an optical cell, the sample space defined by a front plate having a first optical window, a back plate, and a spacer, the sample space having a thermomechanically stable sample gap between the first optical window in the front plate and the back plate,
directing an incident light beam to pass through the first optical window and into the sample space to impinge on the sample;
measuring the spectrum of light transmitted through, reflected by, emitted by, or scattered by the sample;
wherein the sample gap is thermomechanically stable when the temperature of the sample space is varied in a temperature range of experimentation.

41. The method of claim 40, wherein the incident light beam is directed to impinge directly on the sample in the sample space without being reflected by the back plate or by the spacer before impinging on the sample.

42. The method of claim 40, wherein the light transmitted through, reflected by, emitted by, or scattered by the sample is reflected at most once by the back plate or by the spacer while traveling through the sample.

43. The method of claim 40, wherein the incident light beam contains light having a wavelength in the range of from about 0.1 μm to about 50 μm.

44. The method of claim 40, comprising measuring the infrared, visible, or ultraviolet spectrum of light transmitted through, reflected by, emitted by, or scattered by the sample.

45. The method of claim 40, wherein the incident light beam is directed to pass through the first optical window into the sample space with an angle of incidence at an interface between the first optical window and the sample space less than or equal to about 95% of the critical angle.

46. The method of claim 40, wherein a bath fluid in the sample space is exchanged within less than or equal to about 0.2 seconds.

47. The method of claim 40, wherein the sample comprises a solid, comprising separating the spacer from the front plate or from the back plate to place the sample in or to remove the sample from the sample space.

48. The method of claim 40, further comprising providing a heating/cooling element, in contact with the frame; and ramping the temperature of the heating/cooling element according to a predetermined schedule while measuring the spectrum of light transmitted through, reflected by, emitted by, or scattered by the sample.

* * * * *